United States Patent
Braun et al.

(10) Patent No.: US 9,126,972 B2
(45) Date of Patent: Sep. 8, 2015

(54) 2-AMINO-3-(IMIDAZOL-2-YL)-PYRIDIN-4-ONE DERIVATIVES AND THEIR USE AS VEGF RECEPTOR KINASE INHIBITORS

(75) Inventors: Alain Braun, Paris (FR); Olivier Duclos, Paris (FR); Gilbert Lassalle, Paris (FR); Franz Lorge, Paris (FR); Valerie Martin, Paris (FR); Olaf Ritzeler, Franfurt am Main (DE); Aurelie Strub, Paris (FR)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 14/117,750

(22) PCT Filed: May 16, 2012

(86) PCT No.: PCT/EP2012/059145
§ 371 (c)(1),
(2), (4) Date: Nov. 14, 2013

(87) PCT Pub. No.: WO2012/159959
PCT Pub. Date: Nov. 29, 2012

(65) Prior Publication Data
US 2014/0094488 A1   Apr. 3, 2014

(30) Foreign Application Priority Data
May 20, 2011 (EP) .................... 11305624

(51) Int. Cl.
C07D 471/04 (2006.01)
C07D 401/14 (2006.01)
C07D 401/04 (2006.01)
A61K 31/4709 (2006.01)
A61K 31/4375 (2006.01)
A61K 45/06 (2006.01)

(52) U.S. Cl.
CPC .......... *C07D 401/04* (2013.01); *A61K 31/4375* (2013.01); *A61K 31/4709* (2013.01); *A61K 45/06* (2013.01); *C07D 471/04* (2013.01)

(58) Field of Classification Search
CPC .. C07D 471/04; C07D 401/14; C07D 401/04; A61K 31/4709; A61K 31/4375

USPC ............... 514/300, 312; 546/122, 153
See application file for complete search history.

(56) References Cited

U.S. PATENT DOCUMENTS

| 8,436,011 B2 | 5/2013 | Bellevergue et al. |
| 8,470,847 B2 | 6/2013 | Alam et al. |
| 2013/0005724 A1 | 1/2013 | Lassalle et al. |

FOREIGN PATENT DOCUMENTS

| KR | 100744826 B1 | 7/2005 |
| WO | WO-2008/121687 A2 | 10/2008 |
| WO | WO-2008/121687 A3 | 10/2008 |
| WO | WO 2009/007535 A2 | 1/2009 |
| WO | WO 2009/053799 A1 | 4/2009 |
| WO | WO 2010/004197 A2 | 1/2010 |
| WO | WO 2010/073078 A2 | 7/2010 |
| WO | WO 2011/061458 A1 | 5/2011 |

OTHER PUBLICATIONS

Abdel-Meguid; Biochemistry, 1994, 33, 11671-11677.*
International Search Report dated Jun. 29, 2012 issued in PCT/EP2012/059145.
European Search Report dated Jul. 19, 2011 issued in EP 11 30 5624.
Ivy, S.P. et al. (Oct. 2009). "An Overview of Small-Molecule Inhibitors of VEGFR Signaling," *Nature Reviews* 6:569-579.

* cited by examiner

*Primary Examiner* — John Mabry
*Assistant Examiner* — Daniel Carcanague
(74) *Attorney, Agent, or Firm* — Morrison & Foerster LLP

(57) ABSTRACT

The invention relates to the compounds of general formula (I): Preparation process and therapeutic use.

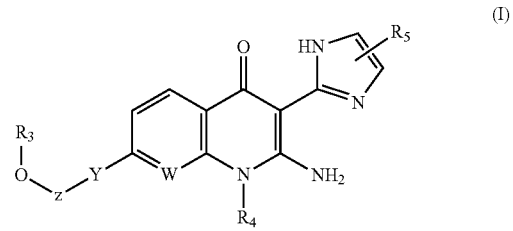

19 Claims, No Drawings

2-AMINO-3-(IMIDAZOL-2-YL)-PYRIDIN-4-ONE DERIVATIVES AND THEIR USE AS VEGF RECEPTOR KINASE INHIBITORS

The present invention relates to a 7-phenol or a 7-alkynyl-3-(imidazol-2-yl)-1,8-naphthyridin-4-one derivatives and their possible quinolinone analogs which are inhibitors of the kinase activity of VEGF receptor, to the preparation thereof and to the therapeutic use thereof.

VEGF (Vascular Endothelial Growth Factor) family of proteins bind to three structurally related receptor tyrosine kinases known as VEGF-R1 (Flt-1), VEGF-R2 (KDR) and VEGF-R3 (Flt-4). All three receptors are vital for the development of the vasculature during embryogenesis and during tumor-induced angiogenesis. In addition, VEGFR-3 plays an important role in the development of the lymphatic system and in tumor induced-lymphangiogenesis Particularly WO 2009/007535 describes substituted 7-alkynyl-4-oxo-1,8-naphthyridin-3-carboxamides derivatives which are inhibitors of the kinase activity of VEGF receptor. The compounds of the present invention differ from these compounds of the prior art at least by the presence of an imidazole ring in position 3 of the bicycle.

Criteria to be taken into account in the development of a drug compound are the exposure of the compound to the tissues and its efficacy. These criteria could be enhanced by improving at least one of the following items among efficacy, absorption, distribution, metabolism, excretion and toxicology."

It remains a need to dispose of inhibitors of the kinase activity VEGF receptor with an enhanced activity and this is advantageously achieved with the novel compounds according to the invention.

A first subject of the invention concerns the compounds corresponding to the general formula (I) hereinbelow.

Another subject of the invention concerns processes for preparing the compounds of general formula (I).

Another subject of the invention concerns the use of the compounds of general formula (I) especially in medicaments or in pharmaceutical compositions.

The compounds of the invention correspond to the general formula (I):

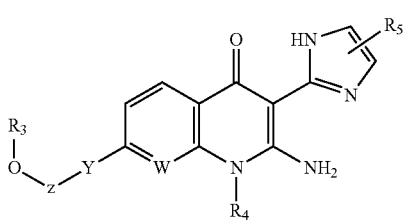

(I)

in which:

W represents a nitrogen atom or a group CH;

Y represents a group $C_2$-$C_3$-alkynylene, a 1,4-phenylene optionally substituted with $R_7$ which represents one or more halogen atom(s);

Z represents a bond or a group $CR_1R_2$;

$R_1$ and $R_2$, independently of each other, represent a group chosen from a hydrogen atom, a group $C_1$-$C_6$-alkyl, a trifluoromethyl group, a group $(CH_2)_nOR_6$, $C_3$-$C_7$-cycloalkyl, an heteroaryl or an aryl optionally substituted with one or more halogen atom(s);

$R_1$ and $R_2$ can form together, with the carbon atom which bear them, a $C_3$-$C_7$-cycloalkyl;

$R_3$ represents a hydrogen atom;

$R_4$ represents a group chosen from a group $C_1$-$C_6$-alkyl, a group $(CH_2)_nOR_6$, $C_3$-$C_7$-cycloalkyl or $C_1$-$C_6$-alkyl optionally substituted by a $C_3$-$C_7$-cycloalkyl;

$R_5$ represents a group chosen from a hydrogen atom or a group $C_1$-$C_6$-alkyl;

$R_6$ represents a group chosen from a hydrogen atom or a group $C_1$-$C_6$-alkyl;

n is equal to 1, 2 or 3.

The compounds of formula (I) may comprise one or more asymmetric carbon atoms. They may thus exist in the form of enantiomers or diastereoisomers. These enantiomers and diastereoisomers, and also mixtures thereof, including racemic mixtures, form part of the invention.

The compounds of formula (I) may exist in the form of bases or of acid-addition salts. Such addition salts form part of the invention.

These salts may be prepared with pharmaceutically acceptable acids, but the salts of other acids that are useful, for example, for purifying or isolating the compounds of formula (I) also form part of the invention.

In the context of the present invention, the following definitions apply:

a halogen atom: a fluorine, a chlorine, a bromine or an iodine atom;

$C_t$-$C_z$: a carbon-based chain possibly containing from t to z carbon atoms in which t and z may take values from 1 to 7; for example, $C_1$-$C_3$ is a carbon-based chain possibly containing from 1 to 3 carbon atoms;

an alkyl: a linear or branched saturated aliphatic group. Examples that may be mentioned include methyl, ethyl, n-propyl, isopropyl, butyl, isobutyl, tert-butyl, pentyl, etc.;

an alkylene: a bivalent radical derived from an alkane, by removal of a hydrogen atom from each of the two terminal carbon atoms of the chain, optionally substituted by an alkyl group; for example a group $C_1$-$C_3$-alkylene represents a linear or branched divalent carbon-based chain of 1 to 3 carbon atoms, more particularly a methylene, ethylene, methylethylene or propylene;

an alkenylene: a bivalent radical derived from an alkene, by removal of a hydrogen atom from each of the two terminal carbon atoms of the chain, optionally substituted by an alkyl or alkenyl group; for example a group $C_2$-$C_3$-alkenylene represents a linear or branched divalent carbon-based chain of 2 to 3 carbon atoms, more particularly an ethenylene or a propenylene;

an alkynylene: a bivalent radical derived from an alkyne, by removal of a hydrogen atom from each of the two terminal carbon atoms of the chain, optionally substituted by an alkyl, an alkenyl or an alkynyl group; for example a group $C_2$-$C_3$-alkynylene represents a linear or branched divalent carbon-based chain of 2 to 3 carbon atoms, more particularly an ethynylene or a propynylene;

a cycloalkyl: a saturated or partially unsaturated cyclic alkyl group. Examples that may be mentioned include the groups cyclopropyl, cyclobutyl, cyclopentyl, cyclohexyl, cyclopropenyl, cyclobutenyl, cyclopentenyl, cyclohexenyl, etc.;

a cycloalkyloxy: a radical —O-cycloalkyl in which the cycloalkyl group is as defined previously;

a fluoroalkyl: an alkyl group, one or more hydrogen atoms of which have been replaced with a fluorine atom;

an alkoxy: a radical —O-alkyl in which the alkyl group is as defined previously;

a fluoroalkoxy: an alkoxy group, one or more hydrogen atoms of which have been replaced with a fluorine atom;

a thioalkyl or alkylthio: a radical —S-alkyl in which the alkyl group is as defined previously;

an aryl: a monocyclic or bicyclic aromatic group containing between 6 and 10 carbon atoms. Examples of aryl groups that may be mentioned include phenyl and naphthyl groups;

an arylene: bivalent group derived from aryl by removal of a hydrogen atom from two ring carbon atoms. Example of arylene group that may be mentioned include phenylene group;

a heterocycle: a saturated or partially unsaturated 5- to 7-membered monocyclic group, comprising from 1 to 3 heteroatoms chosen from O, S and N. Examples of heterocycles that may be mentioned include azetidinyl, piperidyl, azepinyl, morpholinyl, thiomorpholinyl, piperazinyl, homopiperazinyl, dihydrooxazolyl, dihydrothiazolyl, dihydroimidazolyl, dihydropyrrolyl or tetrahydropyridyl, [1,3]dioxolyl, [1,3]dioxinyl, dihydro[1,4]dioxinyl, dihydro[1,2]oxazinyl, dihydro[1,3]oxazinyl, dihydrooxazolyl, dihydroisoxazolyl, dihydro[1,4]oxazinyl, tetrahydro[1,3]oxazepinyl, tetrahydro[1,4]oxazepinyl, tetrahydro[1,3]diazepinyl and tetrahydro[1,4]diazepinyl;

a heteroaryl: a 5- to 12-membered monocyclic or bicyclic aromatic group containing from 1 to 5 heteroatoms chosen from O, S and N. Examples of monocyclic heteroaryls that may be mentioned include imidazolyl, pyrazolyl, thiazolyl, oxazolyl, isothiazolyl, isoxazolyl, furyl, thienyl, oxadiazolyl, thiadiazolyl, triazolyl, tetrazolyl, pyridyl, pyrazinyl, pyrimidinyl, pyridazinyl and triazinyl. Examples of bicyclic heteroaryls that may be mentioned include indolyl, isoindolyl, benzofuryl, benzothiophenyl, benzoxazolyl, benzimidazolyl, indazolyl, benzothienyl, isobenzofuryl, isobenzothiazolyl, pyrrolo[2,3-c]pyridyl, pyrrolo[2,3-b]pyridyl, pyrrolo[3,2-b]pyridyl, pyrrolo[3,2-c]pyridyl, pyrrolo[1,2-a]pyridyl, quinolyl, isoquinolyl, cinnolinyl, quinazolinyl, quinoxalinyl, pyrrolo[1,2-a]imidazolyl, imidazo[1,2-a]pyridyl, imidazo[1,2-a]pyridazinyl, imidazo[1,2-c]pyrimidinyl, imidazo[1,2-a]pyrimidinyl, imidazo[1,2-a]pyrazinyl, imidazo[4,5-b]pyrazinyl, imidazo[4,5-b]pyridyl, imidazo[4,5-c]pyridyl, pyrazolo[2,3-a]pyridyl, pyrazolo[2,3-a]pyrimidinyl, pyrazolo[2,3-a]pyrazinyl, thiazolo[5,4-b]pyridyl, thiazolo[5,4-c]pyridyl, thiazolo[4,5-c]pyridyl, thiazolo[4,5-b]pyridyl, oxazolo[5,4-b]pyridyl, oxazolo[5,4-c]pyridyl, oxazolo[4,5-c]pyridyl, oxazolo[4,5-b]pyridyl, isothiazolo[5,4-b]pyridyl, isothiazolo[5,4-c]pyridyl, isothiazolo[4,5-c]pyridyl, isothiazolo[4,5-b]pyridyl, isoxazolo[5,4-b]pyridyl, isoxazolo[5,4-c]pyridyl, isoxazolo[4,5-c]pyridyl and isoxazolo[4,5-b]pyridyl.

"oxo" means "=O";

"thio" means "—S—".

In the context of the present invention, the following abbreviations and empirical formulae are used:

Boc tert-Butyloxycarbonyl
CuI Copper (I) iodide
$CH_2Cl_2$ Dichloromethane
HPLC High performance liquid chromatography
LC/MS Liquid chromatography/mass spectrometry
dba Dibenzylideneacetone
DCM Dichloromethane
DME Dimethoxyethane
DMF Dimethylformamide
DMSO Dimethylsulphoxide
dppf 1,1'-Bis(diphenylphosphino)ferrocene
° C. degree Celsius
$Et_3N$ Triethylamine
h Hour(s)
HCl Hydrochloric acid
IR Infrared
MeOH Methanol
min. Minutes
ml Milliliter
$MgSO_4$ Magnesium sulphate
NaCl Sodium chloride
$NH_4Cl$ Ammonium chloride
$NH_4OH$ Ammonium hydroxide
$NaHCO_3$ Sodium hydrogen carbonate
$Na_2SO_4$ Sodium sulphate
NMR Nuclear Magnetic Resonance
Rt Retention time
SEM [2-(trimethylsilyl)ethoxy]methyl
THF Tetrahydrofuran
TOSMIC Tosylmethylisocyanide
Trityl Triphenylmethyl
Xphos 2-Dicyclohexylphosphino-2',4',6'-triisopropylbiphenyl Among the compounds of general formula (I) that are subjects of the invention, a first subgroup of compounds is constituted by the compounds for which W represents a nitrogen atom or a group CH.

Among the compounds of general formula (I) that are subjects of the invention, a second subgroup of compounds is constituted by the compounds for which W represents a nitrogen atom.

Among the compounds of general formula (I) that are subjects of the invention, a third subgroup of compounds is constituted by the compounds for which Y represents a group $C_2$-$C_3$-alkynylene, more particularly ethynylene.

Among the compounds of general formula (I) that are subjects of the invention, a fourth subgroup of compounds is constituted by the compounds for which:

Z represents a bond, a group $CR_1R_2$;

$R_1$ represents a group chosen from a hydrogen atom, a group $C_1$-$C_6$-alkyl, a group $(CH_2)_nOR_6$, $C_3$-$C_7$-cycloalkyl, an aryl or a 5- or 6-membered-heteroaryl optionally substituted with one or more halogen atom(s);

$R_2$ represents a group chosen from a hydrogen atom, a group $C_1$-$C_6$-alkyl or a trifluoromethyl;

$R_6$ represents a group chosen from a hydrogen atom or a group $C_1$-$C_6$-alkyl;

n is equal to 1, 2 or 3.

Among the compounds of general formula (I) that are subjects of the invention, a fifth subgroup of compounds is constituted by the compounds for which:

Z represents a group $CR_1R_2$;

$R_1$ represents a group chosen from a hydrogen atom, a group $C_1$-$C_6$-alkyl, a group $(CH_2)_nOR_6$, $C_3$-$C_7$-cycloalkyl, an aryl or a 5- or 6-membered-heteroaryl;

$R_2$ represents a group chosen from a hydrogen atom, a group $C_1$-$C_6$-alkyl or a trifluoromethyl;

$R_6$ represents a group chosen from a hydrogen atom or a group $C_1$-$C_6$-alkyl; and n is equal to 1, 2 or 3.

When Y represents a group $C_2$-$C_3$-alkynylene, more particularly ethynylene, then Z represents a group $CR_1R_2$, $R_1$ and $R_2$ being as defined above.

Among the compounds of general formula (I) that are subjects of the invention, a sixth subgroup of compounds is constituted by the compounds for which $R_4$ represents a group chosen from a group $C_1$-$C_6$-alkyl, a group $(CH_2)_nOR_6$, $C_3$-$C_7$-cycloalkyl or $C_1$-$C_6$-alkyl optionally substituted by a $C_3$-$C_7$-cycloalkyl.

Among the compounds of general formula (I) that are subjects of the invention, a seventh subgroup of compounds is constituted by the compounds for which $R_4$ represents a group $C_1$-$C_6$-alkyl, more particularly an ethyl.

Among the compounds of general formula (I) that are subjects of the invention, a eighth subgroup of compounds is constituted by the compounds for which $R_5$ represents a group chosen from a hydrogen atom or a group $C_1$-$C_6$-alkyl.

Among the compounds of general formula (I) that are subjects of the invention, a ninth subgroup of compounds is constituted by the compounds for which $R_5$ represents a hydrogen atom.

Among the compounds of general formula (I) that are subjects of the invention, a tenth subgroup of compounds is constituted by the compounds for which the definitions of W, Y, Z, $R_3$, $R_4$ and $R_5$ given hereinabove are combined.

Among the compounds of general formula (I) that are subjects of the invention, a eleventh subgroup of compounds is constituted by the compounds for which:
  W represents a nitrogen atom or a group CH;
  Y represents a group $C_2$-$C_3$-alkynylene or a 1,4-phenylene optionally substituted with a halogen atom;
  Z represents a bond, a group $CR_1R_2$;
  $R_1$ represents a group chosen from a hydrogen atom, a group $C_1$-$C_6$-alkyl, a group $(CH_2)_nOR_6$, $C_3$-$C_7$-cycloalkyl, an aryl or a 5- or 6-membered-heteroaryl optionally substituted with a halogen atom;
  $R_2$ represents a group chosen from a hydrogen atom, a group $C_1$-$C_6$-alkyl or a trifluoromethyl;
  $R_3$ represents a hydrogen atom;
  $R_4$ represents a group chosen from a group $C_1$-$C_6$-alkyl, a group $(CH_2)_nOR_6$, $C_3$-$C_7$-cycloalkyl or $C_1$-$C_6$-alkyl optionally substituted by a $C_3$-$C_7$-cycloalkyl;
  $R_5$ represents a group chosen from a hydrogen atom or a group $C_1$-$C_6$-alkyl;
  $R_6$ represents a group chosen from a hydrogen atom or a group $C_1$-$C_6$-alkyl;
  n is equal to 1, 2 or 3.

Among the compounds of general formula (I) that are subjects of the invention, a twelfth subgroup of compounds is constituted by the compounds for which:
  W represents a nitrogen atom or a group CH;
  Y represents a group $C_2$-$C_3$-alkynylene;
  Z represents a group $CR_1R_2$;
  $R_1$ represents a group chosen from a hydrogen atom, a group $C_1$-$C_6$-alkyl, a group $(CH_2)_nOR_6$, $C_3$-$C_7$-cycloalkyl, an aryl or a 5- or 6-membered-heteroaryl optionally substituted with a halogen atom;
  $R_2$ represents a group chosen from a hydrogen atom, a group $C_1$-$C_6$-alkyl or a trifluoromethyl;
  $R_3$ represents a hydrogen atom;
  $R_4$ represents a group chosen from a group $C_1$-$C_6$-alkyl, a group $(CH_2)_nOR_6$, $C_3$-$C_7$-cycloalkyl or $C_1$-$C_6$-alkyl optionally substituted by a $C_3$-$C_7$-cycloalkyl;
  $R_5$ represents a group chosen from a hydrogen atom or a group $C_1$-$C_6$-alkyl;
  $R_6$ represents a group chosen from a hydrogen atom or a group $C_1$-$C_6$-alkyl;
  n is equal to 1, 2 or 3.

Among the compounds of general formula (I) that are subjects of the invention, a thirteenth subgroup of compounds is constituted by the compounds for which $R_1$ and $R_2$ form together, with the carbon atom which bear them, a $C_3$-$C_7$-cycloalkyl.

Of course, each of the subgroups mentioned above may be combined with one or more of the others subgroups and the corresponding compounds are also subjects of the invention.

Among the compounds of general formula (I) that are subjects of the invention, mention may be made especially of the following compounds:

1: 2-Amino-1-ethyl-7-((3R)-3-hydroxy-4-methoxy-3-methyl-but-1-ynyl)-3-(1H-imidazol-2-yl)-1H-[1,8]naphthyridin-4-one
2: 2-Amino-1-propyl-7-((3R)-3-hydroxy-4-methoxy-3-methyl-but-1-ynyl)-3-(1H-imidazol-2-yl)-1H-[1,8]naphthyridin-4-one
3: 2-Amino-7-(3,4-dihydroxy-3-methyl-but-1-ynyl)-1-ethyl-3-(1H-imidazol-2-yl)-1H-[1,8]naphthyridin-4-one
4: 2-Amino-1-ethyl-7-(-3-hydroxy-3-pyridin-2-yl-but-1-ynyl)-3-(1H-imidazol-2-yl)-1H-[1,8]naphthyridin-4-one
5: 2-Amino-1-ethyl-7-[(3R)-3-hydroxy-4-methoxy-3-methylbut-1-yn-1-yl]-3-(4-methyl-1H-imidazol-2-yl)-1,8-naphthyridin-4(1H)-one
6: 2-Amino-1-(cyclopropylmethyl)-7-(3-hydroxypent-1-yn-1-yl)-3-(1H-imidazol-2-yl)-1,8-naphthyridin-4(1H)-one
7: 2-Amino-1-ethyl-7-[(3R)-3-hydroxy-4-methoxy-3-methylbut-1-yn-1-yl]-3-(1H-imidazol-2-yl)quinolin-4(1H)-one
8: 2-Amino-7-(3-chloro-4-hydroxyphenyl)-1-ethyl-3-(1H-imidazol-2-yl)-1,8-naphthyridin-4(1H)-one
9: 2-Amino-1-ethyl-7-[3-(2-fluorophenyl)-3-hydroxybut-1-yn-1-yl]-3-(1H-imidazol-2-yl)-1,8-naphthyridin-4(1H)-one
10: 2-Amino-1-cyclopentyl-7-(3-hydroxypent-1-yn-1-yl)-3-(1H-imidazol-2-yl)-1,8-naphthyridin-4(1H)-one
11: 2-Amino-7-(3-hydroxypent-1-yn-1-yl)-3-(1H-imidazol-2-yl)-1-(3-methoxypropyl)-1,8-naphthyridin-4(1H)-one
12: 2-Amino-7-(3-hydroxypent-1-yn-1-yl)-3-(1H-imidazol-2-yl)-1-(2-methoxyethyl)-1,8-naphthyridin-4(1H)-one
13: 2-Amino-1-ethyl-7-[(1-hydroxycyclobutyl)ethynyl]-3-(1H-imidazol-2-yl)-1,8-naphthyridin-4(1H)-one
14: 2-Amino-1-ethyl-7-[(1-hydroxycyclopentyl)ethynyl]-3-(1H-imidazol-2-yl)-1,8-naphthyridin-4(1H)-one
15: 2-Amino-1-ethyl-7-(3-hydroxy-3-methylbut-1-yn-1-yl)-3-(1H-imidazol-2-yl)-1,8-naphthyridin-4(1H)-one
16: 2-Amino-1-ethyl-7-(3-hydroxy-3-methylpent-1-yn-1-yl)-3-(1H-imidazol-2-yl)-1,8-naphthyridin-4(1H)-one
17: 2-Amino-1-ethyl-7-(3-hydroxy-3-phenylbut-1-yn-1-yl)-3-(1H-imidazol-2-yl)-1,8-naphthyridin-4(1H)-one
18: 2-Amino-1-ethyl-7-[3-(3-fluorophenyl)-3-hydroxybut-1-yn-1-yl]-3-(1H-imidazol-2-yl)-1,8-naphthyridin-4(1H)-one
19: 2-Amino-1-ethyl-3-(1H-imidazol-2-yl)-7-(4,4,4-trifluoro-3-hydroxy-3-phenylbut-1-yn-1-yl)-1,8-naphthyridin-4(1H)-one
20: 2-Amino-7-(3-cyclopropyl-3-hydroxybut-1-yn-1-yl)-1-ethyl-3-(1H-imidazol-2-yl)-1,8-naphthyridin-4(1H)-one
21: 2-Amino-1-ethyl-7-[3-hydroxy-3-(thiophen-2-yl)but-1-yn-1-yl]-3-(1H-imidazol-2-yl)-1,8-naphthyridin-4(1H)-one
22: 2-Amino-1-ethyl-7-(3-hydroxybut-1-yn-1-yl)-3-(1H-imidazol-2-yl)-1,8-naphthyridin-4(1H)-one
23: 2-Amino-1-ethyl-7-(3-hydroxypent-1-yn-1-yl)-3-(1H-imidazol-2-yl)-1,8-naphthyridin-4(1H)-one
24: 2-Amino-1-ethyl-7-(3-hydroxyhex-1-yn-1-yl)-3-(1H-imidazol-2-yl)-1,8-naphthyridin-4(1H)-one
25: 2-Amino-1-ethyl-7-(3-hydroxy-4-methylpent-1-yn-1-yl)-3-(1H-imidazol-2-yl)-1,8-naphthyridin-4(1H)-one 26: 2-Amino-1-ethyl-7-(3-hydroxy-3-phenylprop-1-yn-1-yl)-3-(1H-imidazol-2-yl)-1,8-naphthyridin-4(1H)-one 27: 2-Amino-7-((3R)3,4-dihydroxy-3-methyl-but-1-ynyl)-1-ethyl-3-(1H-imidazol-2-yl)-1,8-naphthyridin-4(1H)-one 28: 2-Amino-7-((3S)3,4-dihydroxy-3-methyl-but-1-ynyl)-1-ethyl-3-(1H-imidazol-2-yl)-1,8-naphthyridin-4(1H)-one 29: 2-Amino-1-ethyl-7-((3S)-3-hydroxy-4-methoxy-3-methyl-but-1-ynyl)-3-(1H-imidazol-2-yl)-1,8-naphthyridin-4(1H)-one In the text hereinbelow, the term "leaving group" means a group that can be readily cleaved from a molecule by breaking a heterolytic bond, with loss of an electron pair. This group may thus be readily replaced by another group during a substitution reaction, for example. Such leaving groups are, for example, halogens or an activated hydroxyl group such as a methanesulfonate, benzenesulfonate, p-toluenesulfonate, triflate, acetate, etc. Examples of leaving groups and references for preparing them are given in "Advances in Organic Chemistry", J. March, 5th Edition, Wiley Interscience, 2001.

In the text hereinbelow, the term "protecting group" (PG) means a group that can be momentarily incorporated into a chemical structure for the purpose of temporarily inactivating a part of the molecule during a reaction, and which may be readily removed in a subsequent synthetic step. Examples of protecting groups and references concerning their properties are given in "Protective Groups in Organic Synthesis", T. W. Greene, P. G. M. Wutz, 3rd Edition, Wiley Interscience 1999.

In accordance with the invention, the compounds of general formula (I) can be prepared according to the process illustrated by the general scheme 1, 2 and 3, below:

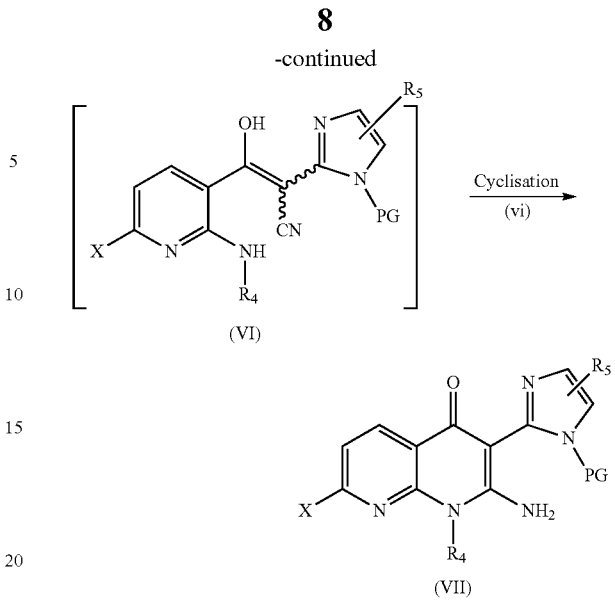

-continued
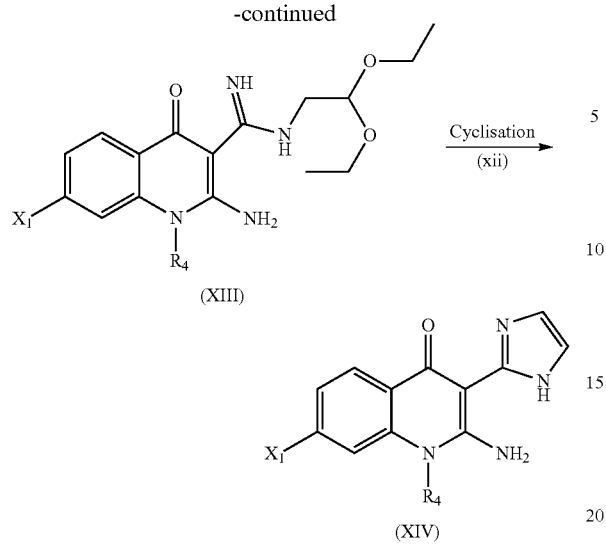

Scheme 3:
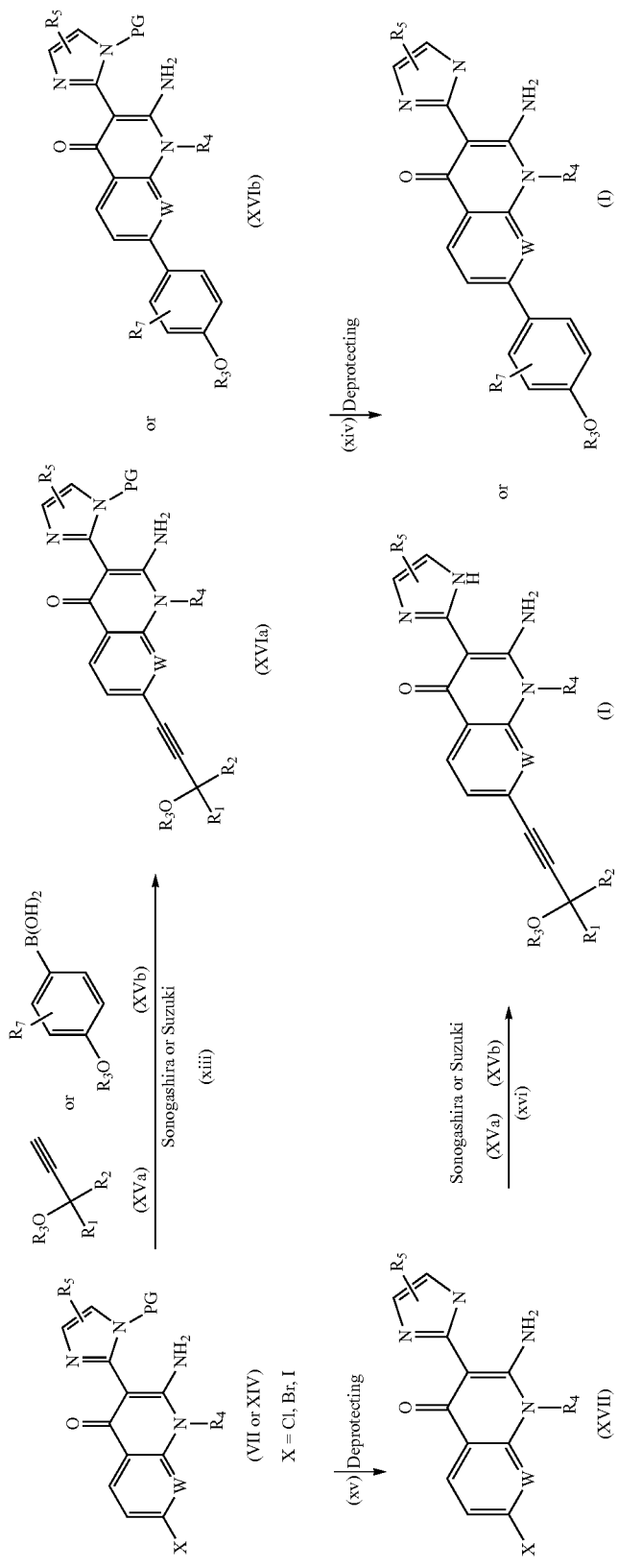

According to scheme 1, in stage (i), a 2,6-dihalogenonicotinic acid of formula (II) is mono-substituted in position 2 with an amine of formula $R_4$—$NH_2$ (where $R_4$ is as defined previously with reference to the compounds of formula (I)), at room temperature, or at a temperature from 50° C. to 100° C., with conventional heating or microwave heating and in a protic solvent such as an alcohol, for example ethanol, n-butanol, tert-butanol or water. The acid (III), resulting from stage (i), is then activated to a derivative of formula (IV), following stage (ii) either in the form of acid fluoride by the action of cyanuryl fluoride at room temperature, in the presence of a base such as triethylamine or pyridine and in an aprotic solvent such as dichloromethane or THF, as described by G. Olah et al., in Synthesis (1973), 487, or in the form of imidazolide by the action of carbonyldiimidazole in a polar aprotic solvent such as DMF or THF or by other methods known by a person skilled in the art, such as those described by Mukaiyama and Tanaka in Chem. Lett. (1976), 303 or by Ishikawa and Sasaki in Chem. Lett. (1976), 1407.

The cyanomethylimidazoles of formula (V) are prepared in two stages from an imidazole-2-carboxaldehyde unsubstituted or substituted in position (4,5) of the imidazole. In stage (iii) the free nitrogen of the imidazole-2-carboxaldehyde is protected by a protecting group, designated PG in scheme 1, for example such as a SEM, Boc or trityl group, in conventional working conditions known by a person skilled in the art, as described for example in "Protective Groups in Organic Synthesis", Greene et al., 3rd Edition (John Wiley & Sons, Inc., New York). If applicable, the two isomers Tau and Pi of the protected imidazole are obtained and used without distinction in the subsequent reactions. The protected imidazole-2-carboxaldehyde is then transformed in stage (iv) to cyanomethylimidazole of formula (V) by reaction of the aldehyde function with the anion of TOSMIC, formed by adding potassium tert-butylate to an anhydrous DME solution of TOSMIC at low temperature (−50° C.), followed by ring opening of the anionic intermediate formed, 4-tosyl-2-oxazoline, then the reaction mixture is heated under reflux in the presence of methanol to permit formation of the acetylnitrile function following the method described by Van Leusen A. et al. (Synthetic Comm, 10(5) 1980, 399-403).

The acid fluoride or the imidazolide of formula (IV) obtained at the end of stage (ii), very reactive but stable, is then reacted, in stage (v), with a cyanomethylimidazole of formula (V), unsubstituted or substituted in position (4,5), in the presence of one equivalent of a base such as sodium hydride or potassium tert-butoxide, in a polar aprotic solvent such as THF or DMF, at a temperature from −5° C. to room temperature, then a second equivalent of the base used is added and the compound of formula (VI) that formed is cyclized in situ, at room temperature, to give the pyridinopyridinone compound of formula (VII), following stage (vi).

According to scheme 2, in stage (vii), a 2,4-dihalogenotoluene of formula (VIII) is oxidized to the corresponding acid derivative (IX) using a strong oxidant such as potassium permanganate at room temperature, or at a temperature from 50° C. to 100° C., with conventional heating or microwave heating and in a protic solvent such as water and in the presence of a base such as pyridine or by other methods known by a person skilled in the art, such as those described in the following patent: U.S. Pat. No. 6,187,950. The acid (IX), resulting from stage (vii), is mono-substituted in position 2 with an amine of formula $R_4$—$NH_2$ (where $R_4$ is as defined previously with reference to the compounds of formula (I)), at room temperature, or at a temperature from 50° C. to 100° C., with conventional heating or microwave heating and in a protic solvent such as an alcohol, for example ethanol, n-butanol, tert-butanol or water. The acid (X), resulting from stage (viii), is then cyclised in benzo-1,3-oxazine-2,4-dione (XI) by action of carbonyldiimidazole or triphosgene at room temperature, or at a temperature from 50° C. to 120° C., with conventional heating or microwave heating and in an aprotic solvent such as DMF, toluene, THF, dioxane. The benzo-1,3-oxazine-2,4-dione (XI) is then treated by malononitrile at room temperature, or at a temperature from 50° C. to 120° C., with conventional heating or microwave heating and in an aprotic solvent such as DMF, toluene, dioxane and in the presence of a base such as triethylamine, or pyridine or by other methods known by a person skilled in the art, such as those described by Iminov et al. in Synthesis (2008) 1535, to obtain nitrile (XII). This nitrile (XII) resulting from stage (x) reacted with aminoacetaldehyde diethylacetal, in the presence of a copper catalyst such as CuCl, at room temperature, or at a temperature from 50° C. to 120° C., with conventional heating or microwave heating and in an aprotic solvent such as DME, DMF, toluene, dioxane. The acetal (XIII) resulting from stage (xi) was then cyclised into imidazole (XIV) using strong acidic conditions such as HCl (12N) at room temperature, or at a temperature from 50° C. to 120° C., with conventional heating or microwave heating and in a protic solvent such as an alcohol, for example ethanol, n-butanol, tert-butanol or water.

To obtain the compounds of formula (I) according to the present invention, two methods, described in scheme 3, can be used starting from halogenated intermediates of formula (VII) or (XIV).

Following the first method leading to a compound of formula (I), which is the subject of the present invention, the halogenated intermediate of formula (VII) or (XIV) is used, in stage (xiii), either in a Sonogashira coupling reaction with a suitable derivative of propargyl alcohol $R_1R_2CH(OR_3)$ $C\equiv CH$ of formula (XVa) where $R_1$, $R_2$ and $R_3$ are as defined previously or in a Suzuki coupling reaction with a suitable aryl boronic acid of formula (XVb). The Sonogashira reaction (xiii) is carried out in the presence of a complex of palladium (in oxidation state (0) or (II)) for example such as $Pd(PPh_3)_4$, $PdCl_2(PPh_3)_2$, in the presence of copper iodide, triethylamine, in an aprotic polar solvent such as THF or DMF, heating conventionally between 80 and 120° C. or by microwave heating.

The Suzuki reaction (xiii) is carried out in the presence of a complex of palladium (in oxidation state (0) or (II)) for example such as $Pd(PPh_3)_4$, $PdCl_2(PPh_3)_2$, $Pd_2dba_3$, Xphos or $PdCl_2(dppf)$, in a protic or aprotic polar solvent such as DME, ethanol, DMF, dioxane, or mixtures of these solvents, in the presence of a base such as cesium carbonate, aqueous sodium hydrogen carbonate, or $K_3PO_4$, heating conventionally between 80 and 120° C. or by microwave heating between 130 and 170° C.

The Sonogashira (XVIa) or Suzuki (XVIb) product are finally deprotected, according to conventional stage of deprotection (xiv), for example in the presence of an acid such as HCl (4N) in dioxane or trifluoroacetic acid in a solvent such as ethanol or dichloromethane, at a temperature between −5° C. and 60° C., to yield compound of formula (I).

Following the second method to obtain a compound of formula (I), which is the subject of the present invention, the halogenated intermediate of formula (VII) or (XIV) is first deprotected (xv), according to the same conventional procedure as for stage (xiv). And the resulting unprotected compound (XVII) is used either in a Sonogashira coupling reaction with a suitable derivative of propargyl alcohol $R_1R_2CH$ $(OR_3)C\equiv CH$ (XVa) where $R_1$, $R_2$ and $R_3$ are as defined previously; or in a Suzuki coupling reaction with a suitable aryl boronic acid of formula (XVb), according to the same conditions as described before for stage (xiii). Both coupling reactions lead directly to compound (I).

If necessary, during the reaction steps presented in scheme 1, the hydroxyl group or certain reactive functions located on the groups $R_1$, $R_2$ and $R_3$ can be temporarily protected with protective groups known to those skilled in the art and as described in "Protective Groups in Organic Synthesis", Greene et al., 2nd Edition (John Wiley & Sons, Inc., New York).

According to another of its aspects, a subject of the invention is also the compounds of formula (VII) as defined in Scheme 1. These compounds can be used as synthesis intermediates for the compounds of formula (I).

According to another of its aspects, a subject of the invention is also the process for preparing a compound of formula (I), characterized in that a compound of formula (VII):

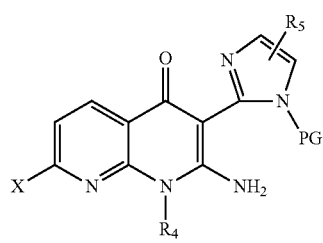

(VII)

in which X is a chlorine or a bromine and $R_4$ and $R_5$ are as defined in the general formula (I), is reacted with a compound of general formula (XVa):

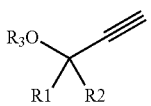

(XVa)

in which $R_1$, $R_2$ and $R_3$ are as defined in the general formula (I),
or is reacted with a compound of general formula (XVb):

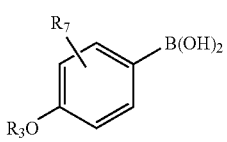

(XVb)

in which $R_3$ and $R_7$ are as defined in the general formula (I),
a conventional stage of deprotection is carried out before or after the reaction of the compound of formula (VII) with the compound of general formula (XVa) or the compound of general formula (XVb).

The examples that follow describe the preparation of certain compounds in accordance with the invention. These examples are not limiting, and serve merely to illustrate the present invention. The illustrated compounds numbers refer to those in Table 1. The elemental microanalyses, the LC/MS analyses and the IR or NMR spectrum confirm the structures of the obtained compounds.

EXAMPLE 1

Compound No 1

2-Amino-1-ethyl-7-((3R)-3-hydroxy-4-methoxy-3-methyl-but-1-ynyl)-3-(1H-imidazol-2-yl)-1H-[1,8]-naphthyridin-4-one 1.1: 6-Chloro-2-ethylamino-nicotinic acid A solution of 18.0 g (84.4 mmol) of 2,6-dichloronicotinic acid in 180 ml of a solution of ethylamine (70% in water) was stirred at ambient temperature for 72 hours. The excess amine was then evaporated off under reduced pressure, and an aqueous solution of acetic acid at 10% was added until the product precipitates. The beige solid was spin-filter-dried, rinsed with cold water and dried in an oven. 10.5 g of the expected product are obtained.
Melting point=158-160° C.
Yield=62%.

1.2: 6-Chloro-2-ethylamino-nicotinoyl fluoride 2 ml (24.8 mmol) of pyridine and 4.2 ml (49.8 mmol) of 2,4,6-trifluorotriazine were added to a suspension of 5.0 g (24.8 mmol) of 6-chloro-2-ethylamino-nicotinic acid in 125 ml of dichloromethane. The mixture was stirred for 3 hours at ambient temperature and then filtered. The solid was rinsed with 50 ml of dichloromethane and the filtrate was washed twice with 60 ml of ice-cold water. The organic phase was dried over $Na_2SO_4$ and the solvent was evaporated off under reduced pressure. 5.01 g of product were obtained in the form of an orange oil which was used without further purification.
Yield=99%.

1.3: 1-(2-Trimethylsilanyl-ethoxymethyl)-1H-imidazole-2-carbaldehyde

An oily suspension of 20.8 g sodium hydride in mineral oil (50%, 0.52 mol) was washed mineral oil free by stirring with hexane 3-times and suspended in 400 ml DMF. Under stirring at ambient temperature 50.0 g (0.520 mol) imidazole-2-carbaldehyde was added to the suspension. After 1.5 h, 101.0 ml (0.572 mol) 2-(trimethylsilanyl)ethoxymethyl chloride was added and the reaction was stirred a further hour. Then excess water was added to the suspension and the reaction mixture was extracted three times with ethyl acetate. The organic phase was dried over $Na_2SO_4$ and the solvent was evaporated off under reduced pressure. The raw material was then purified by column chromatography (DCM) to yield 85.0 g (0.376 mol) of the SEM-protected imidazole-2-carbaldehyde.
Yield=72%.
MH+=227.1 ($C_{10}H_{18}N_2O_2Si$, Mr=226.35).
1H NMR (DMSO-d6, 500 MHz): δ 9.83 (s, 1H); 7.86 (s, 1H); 7.39 (s, 1H); 5.75 (s, 2H); 3.58 (t, 2H); 0.95 (t, 2H); 0.02 (s, 9H).

1:4: [1-(2-Trimethylsilanyl-ethoxymethyl)-1H-imidazol-2-yl]-acetonitrile 1.73 g (8.84 mmol) tosylmethylisocyanide were solved in 10 ml DME and cooled down to −60° C. At this temperature first 1.98 g potassium tert-butoxide was added then slowly a solution of 2.00 g (8.84 mmol) 1-(2-trimethylsilanyl-ethoxymethyl)-1H-imidazole-2-carbaldehyde in 5 ml DME. After 2 hours stirring at −60° C. the reaction was allowed to reach 0° C. and 5 ml methanol (123.60 mmol) was added to the solution. The reaction was stirred for further 24 hours at ambient temperature and for 2 hours at 40° C. Excess water was added and the solution was extracted 3 times with dichloromethane. The organic phase was dried over $Na_2SO_4$, after evaporation of the solvent under reduced pressure the raw material was purified by reverse phase column chromatography (water 0.1% TFA/acetonitrile=80/20 to yield 0.87 g (0.367 mol) of the SEM-protected imidazole-acetonitrile.

Yield=41%

MH+=238.1 ($C_{11}H_{19}N_3OSi$, Mr=237.38).

1H NMR (DMSO-d6, 500 MHz): δ 7.66 (s, 1H); 7.39 (s, 1H); 5.53 (s, 2H); 4.52 (s, 2H); 3.55 (t, 2H); 0.92 (t, 2H); 0.02 (s, 9H).

1.5: 3-(6-Chloro-2-ethylamino-pyridin-3-yl)-3-hydroxy-2-[1-(2-(trimethylsilanyl-ethoxymethyl)-1H-imidazol-2-yl]-acrylonitrile 0.283 g (2.53 mmol) of potassium tert-butylate was added, in small amounts, to a 0° C. solution of 0.600 g (2.53 mmol) [1-(2-trimethylsilanyl-ethoxymethyl)-1H-imidazol-2-yl]-acetonitrile in 10 ml of anhydrous THF. The mixture was stirred for 45 minutes at ambient temperature, and was then cooled again to 0° C. A solution of 0.512 g (2.53 mmol) 6-chloro-2-ethylamino-nicotinoyl fluoride in 10 ml of THF was then added and the medium was stirred at ambient temperature overnight, again cooled down to 0° C. and a second equivalent of potassium tert-butylate (0.283 g, 2.53 mmol) was added. After 2 h stirring at ambient temperature 50 ml saturated ammonium chloride aqueous solution was added, the pH was adjusted to 7 with 2N HCl thereafter then extracted three times with ethyl acetate. The combined organic phases were dried over $MgSO_4$ and the solvents were evaporated under reduced pressure. The raw material is further purified by column chromatography (DCM/Methanol=90:10) yielded 418 mg (yield=38%) of the title compound as an intermediate which was subsequently used in the next step.

MH+=421 ($C_{19}H_{26}ClN_5O_2Si$, Mr=419.99)

1H NMR (DMSO-d6, 500 MHz): δ 13.35 (s, 1H); 7.70 (d, 1H); 7.46 (s, 1H); 7.23 (s, 1H); 7.08 (t, 1H); 6.58 (d, 1H); 5.59 (s, 2H); 3.58 (t, 2H); 3.34 (dq, 2H); 1.13 (t, 3H); −0.03 (3s, 9H).

1.6: 2-Amino-7-chloro-1-ethyl-3-[1-(2-trimethylsilanyl-ethoxymethyl)-1H-imidazol-2-yl]-1H-[1,8]naphthyridin-4-one 0.112 g (1 mmol) of potassium tert-butylate was added, in small amounts, to a 0° C. cold solution of 418 mg (1 mmol) of the intermediate prepared under 1.53-(6-chloro-2-ethylamino-pyridin-3-yl)-3-hydroxy-2-[1-(2-(trimethylsilanyl-ethoxymethyl)-1H-imidazol-2-yl]-acrylonitrile in 5 ml of anhydrous THF. The mixture was stirred for 48 h at ambient temperature after which 50 ml of saturated ammonium chloride aqueous solution was added, the pH is adjusted to 7 with 2N HCl and the reaction mixture was extracted three times with ethyl acetate. The combined organic phases were dried over $MgSO_4$ and the solvents were evaporated under reduced pressure yielding 400 mg of the title compound.

Yield=38%.

MH+=421 ($C_{19}H_{26}ClN_5O_2Si$, Mr=419.99).

1H NMR (DMSO-d6, 500 MHz): δ 8.50 (d, 1H); 8.03 (s, 1H); 7.98 (s, 1H); 7.78 (s, 2H); 7.60 (s, 1H); 5.49 (s, 2H); 4.58 (q, 2H); 3.57 (t, 2H); 1.42 (t, 3H); 0.85 (t, 2H); −0.03 (3s, 9H).

1.7: (±)-2-Methyl-but-3-yne-1,2-diol

A commercially available 0.5 M solution of ethynylmagnesium chloride in tetrahydrofuran was diluted with 200 ml of tetrahydrofuran and cooled to 0° C. Then a solution of hydroxyacetone in 200 ml of tetrahydrofuran is added and the mixture was stirred at ambient temperature for 3 hours. The reaction mixture was cooled and an aqueous solution of $NH_4Cl$ was added. The mixture was extracted 3 times with ethyl acetate and the organic phases were combined, dried over sodium sulphate, filtered, and concentrated under vacuum (approximately 200 mbar). Finally, 20 g of expected product were obtained in the form of a brown oil, which was used without subsequent purification (quantitative crude yield) in the racemic form or could be separated in the pure enantiomers by preparative HPLC on chiral HPLC columns. In order to obtain the optically pure enantiomers, the corresponding racemic mixture was subjected to preparative chromatography on a chiral stationary phase (Chiralpak AD-H column, 250×21 mm, 5 mm) using, as mobile phase: either $CO_2$/2-propanol (70%/30%) with a flow rate of 60 ml/min at a pressure of 100 bar or an isohexane/ethanol (70/30) mixture with 0.3% of TFA and a flow rate of 120 ml/min.

After elution and evaporation, each enantiomer was isolated, and the chemical purity and enantiomeric purity of each are determined by analytical methods known to those skilled in the art.

1.8: 2-Amino-1-ethyl-7-((3R)-3-hydroxy-4-methoxy-3-methyl-but-1-ynyl)-3-[1-(2-trimethylsilanyl-ethoxymethyl)-1H-imidazol-2-yl]-1H-[1,8]naphthyridin-4-one In an argon filled microwave reaction flask 500 mg (1.2 mmol) 2-amino-7-chloro-1-ethyl-3-[1-(2-trimethylsilanyl-ethoxymethyl)-1H-imidazol-2-yl]-1H-[1,8]naphthyridin-4-one, 204 mg (1.8 mmol) (3R)-1-methoxy-2-methyl-but-3-yn-2-ol, 84 mg (0.120 mmol) bis(triphenylphosphine)palladium (II) dichloride, 30 mg (0.16 mmol) copper (I) iodide, 2 ml DMF (degassed), 2 ml triethylamine (degassed) were given and irradiated in the microwave in such a way that the reaction mixture was kept at 120° C. for 24 h. The solvents were evaporated and the solid resuspended in 3 ml DMF and filtrated. The filtrate was then purified by HPLC yielding 430 mg (0.702 mmol) of the TFA salt of the title compound.

Yield=59%.

MH+=498.2 ($C_{25}H_{35}N_5O_4Si$, Mr=497.67).

1H NMR (DMSO-d6, 500 MHz): δ 8.39 (d, 1H); 7.95 (s, 1H); 7.88 (s, 1H); 7.60 (s, 2H); 7.48 (d, 1H); 5.25 (s, 2H); 4.50 (broad signal, 2H); 3.52-3.40 (broad signal, water peak+4H); 1.48 (s, 3H); 1.25 (t, 3H); −0.12 (3s, 9H).

1.9: 2-Amino-1-ethyl-7-((3R)-3-hydroxy-4-methoxy-3-methyl-but-1-ynyl)-3-(1H-imidazol-2-yl)-1H-[1,8]naphthyridin-4-one 240 mg (0.4 mmol) SEM protected naphthyridinone 1.8 was solved at 0° C. in 1.2 ml TFA and 1.2 ml DCM. The solution was kept at 3-5° C. overnight until analytical HPLC showed complete deprotection of the naphthyridinone. The solution is neutralized by adding an excess of aqueous $NaHCO_3$ solution. The mixture was then extracted three times with ethyl acetate. The combined organic phases were dried over $MgSO_4$ and the solvents were evaporated off under reduced pressure. The so gained raw material was purified on silica gel (DCM:MeOH=4:1) yielding 143 mg (quantitative yield) of the unprotected title compound.

MH+=368.2 ($C_{19}H_{21}N_5O_3$, Mr=367.41).

1H NMR (DMSO-d6, 500 MHz): δ 13.15 (s, 1H); 11.55 (b s, 1H); 8.59 (d, 1H); 8.10 (b s, 1H); 7.47 (d, 1H); 7.25 (s, 1H);

7.02 (s, 1H); 5.85 (s, 1H); 4.58 (broad signal, 2H); 3.51-3.370 (broad signal, water peak+4H); 1.48 (s, 3H); 1.25 (t, 3H).

Rt (analytical HPLC): 4.806 min.

EXAMPLE 2

Compound No 2

2-Amino-1-propyl-7-((3R)-3-hydroxy-4-methoxy-3-methyl-but-1-ynyl)-3-(1H-imidazol-2-yl)-1H-[1,8]naphthyridin-4-one Using the procedure described up to step 1.6, 2-amino-7-chloro-1-propyl-3-[1-(2-trimethylsilanyl-ethoxymethyl)-1H-imidazol-2-yl]-1H-[1,8]naphthyridin-4-one was synthesized by using n-propylamine instead of ethylamine in step 1.1. Coupling this intermediate to (3R)-1-methoxy-2-methyl-but-3-yn-2-ol following in an analogous manner to the detailed procedure outlined for example 1 the title compound was accessed.

MH+=382.48 ($C_{20}H_{23}N_5O_3$, Mr=381.44).

1H NMR (DMSO-d6, 500 MHz): δ broad signals: 8.45 (m, 1H); 7.4 (m, 3H); 5.85 (s, 1H); 4.58 (m, 3H); 3.51-3.370 (water peak+4H); 1.70 (m, 2H); sharp signals: 1.48 (s, 3H); 0.95 (t, 3H).

Rt (analytical HPLC): 4.98 min.

EXAMPLE 3

Compound No 3, No 27 and No 28

2-Amino-7-(3,4-dihydroxy-3-methyl-but-1-ynyl)-1-ethyl-3-(1H-imidazol-2-yl)-1,8-naphthyridin-4(1H)-one 2-Amino-7-((3R)3,4-dihydroxy-3-methyl-but-1-ynyl)-1-ethyl-3-(1H-imidazol-2-yl)-1,8-naphthyridin-4(1H)-one 2-Amino-7-((3S)3,4-dihydroxy-3-methyl-but-1-ynyl)-1-ethyl-3-(1H-imidazol-2-yl)-1,8-naphthyridin-4(1H)-one 3.1. 2-Amino-1-ethyl-7-(3,4-dihydroxy-3-methyl-but-1-ynyl)-1-ethyl-3-[1-(2-trimethylsilanyl-ethoxymethyl)-1H-imidazol-2-yl]-1,8-naphthyridin-4(1H)-one Following the detailed procedure outlined for step 1.8, using the intermediate described under 1.6 (2-amino-7-chloro-1-ethyl-3-[1-(2-trimethylsilanyl-ethoxymethyl)-1H-imidazol-2-yl-1,8-naphthyridin-4(1H)-one) and the (±)-2-methyl-but-3-yne-1,2-diol, previously prepared as in procedure describe in step 1.7, was accessed.

MH+=354.16 ($C_{18}H_{19}N_5O_3$, Mr=353.38)

Rt (analytical HPLC): 4.483 min.

3.2. 2-Amino-1-ethyl-7-((3R)3,4-dihydroxy-3-methyl-but-1-ynyl)-1-ethyl 3-[1-(2-trimethylsilanyl-ethoxymethyl)-1H-imidazol-2-yl]-1,8-naphthyridin-4(1H)-one 2-Amino-1-ethyl-7-((3S)3,4-dihydroxy-3-methyl-but-1-ynyl)-1-ethyl-3-[1-(2-trimethylsilanyl-ethoxymethyl)-1H-imidazol-2-yl]-1,8-naphthyridin-4(1H)-one The racemic compound obtains at step 3.1 was subjected to a preparative Chiral SFC purification, using a methods, Berger prep SFC, UV détection at 230 nm, stationary phase Chiralpak IC 20×250 nm 5 µm, mobile phase 65%/35% CO2/(MeOH+à.5% isopropylamine), 50 ml/min, 100 bars) leading to the separation of the two enantiomers.

For the two enantiomers the chiral purity was controlled using Chiral SFC methods, Berger SFC, UV détection at 210 nm, stationary phase Chiralpak AD-H (250 mm×4.6) 5 µm, mobile phase 65/35% CO2/(isopropanol+0.5% isopropylamine), 2.4 ml/min, 100 bars.

R enantiomer (tr=6.9 min, enatiomeric purity=97.9%)

S enantiomer (tr=5.9 min, enatiomeric purity=96.8%)

3.3. 2-Amino-7-(3,4-dihydroxy-3-methyl-but-1-ynyl)-1-ethyl-3-(1H-imidazol-2-yl)-1,8-naphthyridin-4(1H)-one 2-Amino-7-((3R)3,4-dihydroxy-3-methyl-but-1-ynyl)-1-ethyl-3-(1H-imidazol-2-yl)-1,8-naphthyridin-4(1H)-one 2-Amino-7-((3S)3,4-dihydroxy-3-methyl-but-1-ynyl)-1-ethyl-3-(1H-imidazol-2-yl)-1,8-naphthyridin-4(1H)-one After the deprotection step according to step 1.9 compounds 3, 27 and 28 are isolated as a yellow powder.

MH+=354.16 ($C_{18}H_{19}N_5O_3$, Mr=353.38)

Tr=0.77 min

1H NMR (DMSO-d6, 400 MHz): δ 13.15 (s, 1H); 11.55 (bs, 1H); 8.55 (d, 1H, J=6.4 Hz); 8.10 (bs, 1H); 7.47 (d, 1H, J=6.4 Hz); 7.15 (s, 1H); 7.02 (s, 1H); 5.6 (s, 1H); 5.1 (t, 1H, J=6.4 Hz) 4.53 (bd, 2H); 3.49 (dd, 1H, J=6.4; 10.4 Hz); 3.41 (dd, 1H, J=6.4; 10.4 Hz) 1.48 (s, 3H); 1.27 (t, 3H, J=7.2 Hz).

For the two enantiomers the chiral purity was controlled using Chiral SFC methods, Berger SFC, UV détection at 230 nm, stationary phase Chiralpak AD-H (250 mm×4.6) 5 µm, mobile phase 60/40% CO2/(isopropanol+0.5% isopropylamine), 2.4 ml/min, 100 bars.

R enantiomer (tr=8.37 min, enatiomeric purity=99.2%)

S enantiomer (tr=7.29 min, enatiomeric purity=98.5%)

EXAMPLE 4

Compound No 4

2-Amino-1-ethyl-7-(3-hydroxy-3-pyridin-2-yl-but-1-ynyl)-3-(1H-imidazol-2-yl)-1H-[1,8]naphthyridin-4-one Using the intermediate described under 1.6 (2-amino-7-chloro-1-ethyl-3-[1-(2-trimethylsilanyl-ethoxymethyl)-1H-imidazol-2-yl]-1H-[1,8]naphthyridin-4-one) and coupling it to (±)-2-pyridin-2-yl-but-3-yn-2-ol following the detailed procedure outlined for example 1 in an analogous manner the title compound was accessed.

MH+=401.21 ($C_{22}H_{20}N_6O_2$, Mr=400.44).

Rt (analytical HPLC): 4.49 min.

EXAMPLE 5

Compound No 5

2-Amino-1-ethyl-7-[(3R)-3-hydroxy-4-methoxy-3-methyl-but-1-yn-1-yl]-3-(4-methyl-1H-imidazol-2-yl)-1H-[1,8]naphthyridin-4-one 5.1: 4-Methyl-1-(2-trimethylsilanyl-ethoxymethyl)-1H-imidazole-2-carbaldehyde Using the same procedure as for example 1 stage 1.3, starting from 4 g (36.3 mmol) 4(5)-methyl-1H-imidazole-2- carb aldehyde, 1.5 g (38 mmol) of sodium hydride and 6.7 g (40 mmol) 2-(trimethylsilanyl)ethoxymethyl chloride in 73 ml DMF, 8.7 g of the title compound was accessed as a brown oil (quantitative yield).
MH+=241 ($C_{11}H_{20}N_2O_2Si$, 240.377).

5.2: [4-Methyl-1-(2-trimethylsilanyl-ethoxymethyl)-1H-imidazol-2-yl]-acetonitrile Same procedure as that described in example 1, stage 1.4, starting from 8.7 g (32.7 mmol) of 4-methyl-1-(2-trimethylsilanyl-ethoxymethyl)-1H-imidazole-2-carbaldehyde, 6.7 g (34.3 mmol) of TOSMIC and 7.3 g (65 mmol) of potassium tert-butylate in solution in anhydrous DME (54 ml). 6.6 g of compound is obtained in the form of a yellow oil as 70/30 mixture of regioisomers tau and Pi.
Yield=80%.
MH+=252 ($C_{12}H_{21}N_3OSi$, 251.404).
Tr=6.38 and 6.55 min.

5.3: 2-Amino-7-chloro-1-ethyl-3-[4-methyl-1-(2-trimethylsilanyl-ethoxymethyl)-1H-imidazol-2-yl]-1H-[1,8]naphthyridin-4-one Same procedure as that described in example 1, stage (1.5-1.6), starting from 6.3 g (25 mmol) of the compound obtained at the end of stage 6.2, 5 g (25 mmol) of the compound obtained at the end of stage 1.2 and 7.2 g (62 mmol) of potassium tert-butylate in solution in anhydrous THF (83 ml). 4 g of product, in the form of a beige powder, is obtained as a mixture of 80/20 of the 2 isomers Tau □ and Pi, used as a mixture in the next step
Yield=38%.
Melting point=120° C.
MH+=435 ($C_{20}H_{28}ClN_5O_2Si$, 434.013).
Tr=10.5 and 10.6 min,
1H NMR of both isomers (500 MHz, DMSO-d6) δ ppm 8.45 (d, J=8.07 Hz, 2H) 7.70 (b. s., 2H) 7.56 (b. s., 2H) 7.43 (d, J=8.07 Hz, 1H) 7.42 (d, J=8.07 Hz, 1H) 6.99 (m, 1H) 6.84 (m, 1H) 5.18 (s, 2H) 5.17 (s, 2H) 4.43 (q, J=6.85 Hz, 4H) 3.19 (m, 2H) 3.12 (m, 2H) 2.25 (d, J=0.98 Hz, 3H) 2.16 (d, J=0.98 Hz, 3H) 1.24-1.29 (m, 6H) 0.57-0.64 (m, 4H) −0.22 (s, 9H) −0.22 (s, 9H)

5.4: 2-Amino-1-ethyl-7-[(3R)-3-hydroxy-4-methoxy-3-methyl-but-1-yn-1-yl]-3-[4-methyl-1-(2-trimethylsilanyl-ethoxymethyl)-1H-imidazol-2-yl]-1H-[1,8]naphthyridin-4-one In a argon filled microwave reaction flask 0.5 g (1.15 mmol) of the compound obtained at the end of stage 5.3, 0.26 g (2.3 mmol) (R)-1-methoxy-2-methyl-but-3-yn-2-ol, 40 mg (0.06 mmol) bis(triphenylphosphine)palladium (II) dichloride, 22 mg (0.12 mmol) copper (I) iodide, 3 ml DMF (degassed), 3 ml triethylamine (degassed) were heated at 80° C. for 3 h. The solvents were evaporated; the solid was dissolved in ethyl acetate and washed successively with an aqueous solution of saturated $NaHCO_3$ and with HCl (1N). The organic phase was then dried over $Na_2SO_4$, filtrated and concentrated under reduced pressure. The residue was then purified by flash chromatography on silica gel (DCM/THF 95/5: MeOH (1% $NH_4OH$) from 0% to 10%) yielding 0.19 g of the title compound.
Yield: 32%.
MH+=512 ($C_{26}H_{37}N_5O_4Si$, 511.695).
1H NMR (400 MHz, DMSO-d6) δ ppm 8.43 (d, J=7.91 Hz, 2H) 7.69 (br. s., 2H) 7.55 (br. s., 2H) 7.41 (d, J=7.79 Hz, 2H) 6.99 (s, 1H) 6.84 (s, 1H) 5.81 (s, 2H) 5.18 (s, 4H) 4.40-4.58 (m, 4H) 3.47 (d, J=9.54 Hz, 2H) 3.37-3.43 (m, 8H) 3.19 (t, J=8.02 Hz, 2H) 3.12 (t, J=8.08 Hz, 2H) 2.26 (s, 3H) 2.17 (s, 3H) 1.47 (s, 6H) 1.26 (t, J=6.57 Hz, 6H) 0.54-0.67 (m, 4H) −0.23 (s, 18H)

5.5: 2-Amino-1-ethyl-7-[(3R)-3-hydroxy-4-methoxy-3-methyl-but-1-yn-1-yl]-3-(4-methyl-1H-imidazol-2-yl)-1H-[1,8]naphthyridin-4-one 0.18 g (0.36 mmol) of the compound obtained at the end of stage 5.4 was dissolved at 0° C. in 1.7 ml TFA and 1.7 ml DCM. The solution was kept at 3-5° C. overnight. The solution is neutralized by adding an excess of aqueous $NaHCO_3$ solution. The mixture was then extracted three times with ethyl acetate. The combined organic phases were dried over $Na_2SO_4$ and the solvents were evaporated off under reduced pressure. The raw material was purified by crystallization in DCM 62 mg (yield 46%) of the unprotected title compound.
MH+=382 ($C_{20}H_{23}N_5O_3$, 381.434).
1H NMR (DMSO-d6, 500 MHz): (the 2 topoisomers on the imidazole are detected as 60/40 ratio) δ=12.9-12.8 (2s, 1H) 11.6 (brs, 1H) 8.52 (d, J=7.9 Hz, 1H) 8.0 (brs, 1H) 7.42 (d, J=7.9 Hz, 1H) 6.84-6.70 (2s, 1H) 5.8 (s, 1H) 4.56 (m, 2H) 3.46 (d, J=9.5 Hz, 1H) 3.3 (s, 3H) 3.4 (d, J=9.5 Hz, 1H) 2.28-2.2 (2s 3H) 1.47 (s, 3H) 1.28 (t, J=6.6 Hz, 3H)

EXAMPLE 6

Compound No 6

2-Amino-1-cyclopropylmethyl-7-(3-hydroxy-pent-1-ynyl)-3-(1H-imidazol-2-yl)-1H-[1,8]naphthyridin-4-one

6.1: 6-Chloro-2-(cyclopropylmethyl-amino)-nicotinic acid

In a sealable tube, 3 g (42 mmol) of cyclopropylmethylamine is added to 3 g (14 mmol) of 2,6-dichloronicotinic acid in solution in tert-butanol (14 ml), the tube is sealed and heated at 170° C. for 30 minutes in a Biotage Initiator microwave. The reaction mixture is cooled to room temperature, diluted in dichloromethane (100 ml) and washed with a 10% aqueous solution of acetic acid (12 ml). The organic phase is dried over $Na_2SO_4$, filtered, concentrated and dried under vacuum. 3.4 g of product is obtained in the form of an orange oil.
Yield is quantitative.
MH+=227.
Tr=4.54 min.

6.2: 6-Chloro-2-(cyclopropylmethyl-amino)-nicotinoyl fluoride

Same procedure as that described in example 1, stage 1.2, starting from 0.334 g (1.4 mmol) of the compound obtained at the end of stage 7.1 in solution in 4 ml of dichloromethane, 0.38 g (2.8 mmol) of cyanuric fluoride, and 0.28 g (2.8 mmol) of triethylamine. The product, obtained in the form of a green oil, is used without purification in the next stage.

6.3: 2-Amino-7-chloro-1-(cyclopropylmethyl)-3-[1-(2-trimethylsilanyl-ethoxymethyl)-1H-imidazol-2-yl]-1H-[1,8]naphthyridin-4-one Same procedure as that described in example 1, stage (1.5-1.6), starting from the raw compound obtained at the end of stage 6.2, 0.32 g (1.4 mmol) of the compound obtained at the end of stage 1.3 in solution in 5 ml of anhydrous THF and 0.4 g (0.35 mmol) of potassium tert-butylate. 0.56 g of product is obtained in as a brown powder.
Yield=90%.
Melting point=70° C.
MH+=447 ($C_{21}H_{28}ClN_5O_2Si$).
Tr=6.68 min.
1H NMR (400 MHz, DMSO-d6) δ ppm 8.46 (d, J=8.05 Hz, 1H) 7.67 (br. s, 2H) 7.43 (d, J=8.05 Hz, 1H) 7.35 (d, J=1.37 Hz, 1H) 7.12 (d, J=1.19 Hz, 1H) 5.27 (s, 2H) 4.38 (d, J=7.04 Hz, 2H) 3.19-3.25 (m, 2H) 1.21-1.32 (m, 1H) 0.59-0.68 (m, 2H) 0.45-0.57 (m, 4H) −0.21 (s, 9H)

6.4: 2-Amino-1-(cyclopropylmethyl)-7-(3-hydroxy-pent-1-ynyl)-3-[1-(2-trimethylsilanyl-ethoxymethyl)-1H-imidazol-2-yl]-1H-[1,8]naphthyridin-4-one Same procedure as that described in example 5, stage 5.4, starting from 0.5 g (1.2 mmol) of the compound obtained at the end of stage 6.3, 0.22 g (2.5 mmol) pent-4-yn-3-ol, 43 mg (0.06 mmol) bis(triphenylphosphine)palladium (II) dichloride, 23 mg (0.12 mmol) copper (I) iodide, 3 ml DMF (degassed), 3 ml triethylamine (degassed). 0.19 g of the title compound is obtained.
Yield=30%.
MH+=494 ($C_{26}H_{35}N_5O_3Si$ 493.68).
1H NMR (400 MHz, DMSO-d6) δ ppm 8.44 (d, J=7.87 Hz, 1H) 7.65 (br. s, 2H) 7.42 (d, J=7.87 Hz, 1H) 7.33 (s, 1H) 7.10 (s, 1H) 5.63 (d, J=5.58 Hz, 1H) 5.28 (s, 2H) 4.38-4.52 (m, 3H) 3.17-3.25 (m, 2H) 1.67-1.76 (m, 2H) 1.22-1.31 (m, 1H) 1.01 (t, J=7.36 Hz, 3H) 0.59-0.66 (m, 2H) 0.44-0.57 (m, 4H) −0.24-0.20 (m, 9H)

6.5: 2-Amino-1-cyclopropylmethyl-7-(3-hydroxy-pent-1-ynyl)-3-(1H-imidazol-2-yl)-1H-[1,8]naphthyridin-4-one Same procedure as that described in example 5, stage 5.5, starting from 0.18 g (0.36 mmol) of the compound obtained at the end of stage 7.4, in 1.7 ml TFA and 1.7 ml DCM, 19 mg of the title compound is obtained.
Yield=15%
Melting point=252° C.
MH+=364 ($C_{20}H_{21}N_5O_2$, 363.419).
1H NMR (400 MHz, DMSO-d6) δ ppm 13.15 (br s, 1H) 11.5 (br s, 1H) 8.56 (d, J=7.9 Hz, 1H) 8.0 (br. s, 1H) 7.45 (d, J=7.9 Hz, 1H) 7.15 (m, 2H) 5.62 (br s, 1H) 4.62 (m, 2H+1H) 1.75 (m, 2H) 1.34 (m, 1H) 1.05 (t, J=7.36 Hz, 3H) 0.5 (m, 2H) 0.48-(m, 2H).

EXAMPLE 7

Compound No 7

2-Amino-1-ethyl-7-((R)-3-hydroxy-4-methoxy-3-methyl-but-1-ynyl)-3-(1H-imidazol-2-yl)-1H-quinolin-4-one

7.1: 2-Fluoro-4-iodo-benzoic acid 13.39 g (84.74 mmol) potassium permanganate were added to a suspension of 5 g (21.18 mmol) of 2-fluoro-4-iodotoluene and 25.13 g (317.77 mmol) of pyridin in water. The mixture was heated and stirred at 70° C. during 18 hours. As the reaction was not finished, 3.34 g (21.18 mmol) of potassium permanganate were added to the reaction mixture at room temperature and the mixture was stirred for another 6 hours at 70° C. The reaction mixture was then filtered through a celite pad, which was then washed with water and ethyl acetate. After decantation, the aqueous phase was acidified to pH=1 with an aqueous solution of HCl 6N. A white solid was first filtered and the aqueous phase extracted three times with ethyl acetate. The combined organic phases were dried over $MgSO_4$ and the solvents were evaporated off under reduced pressure. The filtered white solid and the solid extracted with ethyl acetate were combined to give 4.1 g.
Yield=73%.
MH+=266.9 ($C_7H_4FIO_2$).
1H NMR (DMSO-d6, 400 MHz): δ 13.49 (broad signal, 1H); 7.88 (d, 1H); 7.78 (d, 1H); 7.65 (d, 1H).

7.2: 2-Ethylamino-4-iodo-benzoic acid 3.5 g (13.16 mmol) of 2-fluoro-4-iodobenzoic acid were mixed to a 16.11 ml solution of ethylamine (70% in water) in a sealed tube. The reaction vessel was heated and stirred at 125° C. during 24 hours. Nitrogen was bubbled through the reaction mixture to eliminate the excess of ethylamine. The reaction mixture was than poured into an iced water solution and the mixture acidified to pH=3-4 with acetic acid. The resulting white solid was then filtered off, washed with water and dried to give 2.2 g (7.55 mmol).
Yield=58%.
MH+=291.8 ($C_9H_{10}INO_2$).
1H NMR (DMSO-d6, 400 MHz): δ 12.5 (br s, 1H); 7.55 (d, 1H); 7.11 (s, 1H); 6.9 (d, 1H).

7.3: 1-Ethyl-7-iodo-1H-benzo[d][1,3]oxazine-2,4-dione 0.785 g (2.65 mmol) of triphosgene were added at room temperature to 2.2 g (7.55 mmol) of 2-ethylamino-4-iodo-benzoic acid in 30 ml of dioxane. The reaction mixture was then heated and stirred at 110° C. during 2 hours. The solution was evaporated to dryness and reevaporated twice after 2 additions of 20 ml of toluene to give 2.39 g (7.5 mmol) of a solid.
Yield=100%.
MH+=317.7 ($C_{10}H_8INO_3$).
1H NMR (DMSO-d6, 400 MHz): δ 7.87 (s, 1H); 7.68 (s, 2H); 4.04 (m, 2H); 1.19 (t, 3H).

7.4: 2-Amino-1-ethyl-7-iodo-4-oxo-1,4-dihydro-quinoline-3-carbonitrile 0.32 g (6.31 mmol) of malononitrile and 1.45 g (14.35 mmol) triethylamine were added to 2 g (6.31 mmol) of 1-ethyl-7-iodo-1H-benzo[d][1,3]oxazine-2,4-dione dissolved in 25 mL of DMF. The solution was stirred for 2 hours at 120° C. and after addition of 0.73 g (7.17 mmol) of triethylamine, for another 1 hour at 110° C. The DMF was then evaporated under reduced pressure and the residue taken over with a mixture of water and dichloromethane. Filtration of this mixture gave a first fraction of the expected compound: 0.55 g (1.62 mmol).
Yield=26%.
MH+=339.7 ($C_{10}H_8INO_3$).
1H NMR (DMSO-d6, 400 MHz): δ 7.99 (s, 1H); 7.80 (d, 1H); 7.7 (m, 2H); 4.21 (m, 2H); 1.20 (t, 3H).

7.5: 2-Amino-N-(2,2-diethoxy-ethyl)-1-ethyl-7-iodo-4-oxo-1,4-dihydro-quinoline-3-carboxamidine 0.38 g (2.86 mmol) of aminoacetaldehyde diethylacetal and 0.155 g (1.57 mmol) of CuCl were added to 0.48 .g (1.43 mmol) of 2-amino-1-ethyl-7-iodo-4-oxo-1,4-dihydro-quinoline-3-carbonitrile dissolved in 20 ml of DME. The solution was stirred and irradiated with microwaves for 0.5 hour at 100° C.

The solution was then filtered off and evaporated to dryness. The raw material was then purified by column chromatography (DCM/MeOH: 9/1) to yield 0.57 g (1.2 mmol) of a solid.
Yield=78%.
MH+=473 ($C_{18}H_{25}IN_4O_3$).

7.6: 2-Amino-1-ethyl-3-(1H-imidazol-2-yl)-7-iodo-1H-quinolin-4-one 0.37 ml of a 12N HCl solution were added at 0° C. to a suspension of 0.13 .g (0.28 mmol) of 2-amino-N-(2,2-diethoxy-ethyl)-1-ethyl-7-iodo-4-oxo-1,4-dihydro-quinoline-3-carboxamidine. The reaction mixture was stirred at room temperature during 16 hours. The reaction mixture was than diluted with 0.55 ml of water, basified with 0.32 ml of 1N NaOH solution, and 0.134 ml of an $NH_4OH$ solution. The mixture was then filtered and the resulting solid was washed with water, acetonitrile and pentane to give 0.08 g (0.21 mmol) of a brown solid.
Yield=76%.
MH+=381 ($C_{14}H_{13}IN_4O$).

7.7: 2-Amino-1-ethyl-7-((R)-3-hydroxy-4-methoxy-3-methyl-but-1-ynyl)-3-(1H-imidazol-2-yl)-1H-quinolin-4-one 0.43 mg (1.15 mmol) of 2-amino-1-ethyl-3-(1H-imidazol-2-yl)-7-iodo-1H-quinolin-4-one, 0.262 (23 mmol) of (R)-3-hydroxy-4-methoxy-3-methyl-but-1-yne, and 0.397 g (3.45 mmol) were mixed in 15 ml of DMF. Argon was flushed through this solution for 10 minutes. After addition of 0.126 mg (0.17 mmol) of 1,1'-bis(diphenylphosphino)ferrocene palladium dichloride and 0.033 mg (0.17 mmol) of copper iodide, the reaction mixture was stirred at 80° C. during 6 hours. The reaction mixture was then evaporated to dryness and the residue poured into a mixture of DCM and water. A black insoluble solid was filtered off (100 mg). The aqueous phase was extracted three times with dichloromethane. The combined organic phases were dried over MgSO4 and the solvents were evaporated off under reduced pressure. The residue was then purified by column chromatography (DCM/MeOH/NH4OH aq: 9/1/0.1) to yield 0.80 g (1.2 mmol) of yellow solid. This solid was recrystallized in dichloromethane to yield 0.02 g of a beige solid.
Yield=4.5%.
MH+=367 ($C_{20}H_{22}N_4O_3$, 366.419).
1H NMR (DMSO-d6, 400 MHz): δ 13.19 (s, 1H); 8.27 (d, 1H); 7.61 (s, 1H); 7.31 (d, 1H); 7.13 (s, 1H); 7.02 (s, 1H); 6.94 (broad signal, 2H); 4.36-4.28 (broad signal, 2H); 3.45-3.25 (broad signal, water peak+4H); 1.46 (s, 3H); 1.31 (t, 3H)

EXAMPLE 8

Compound No 8

2-Amino-7-(3-chloro-4-hydroxy-phenyl)-1-ethyl-3-(1H-imidazol-2-yl)-1H-[1,8]naphthyridin-4-one 8.1: 2-Amino-7-(3-chloro-4-hydroxy-phenyl)-1-ethyl-3-[1-(2-trimethylsilanyl-ethoxymethyl)-1H-imidazol-2-yl]-1H-[1,8]naphthyridin-4-one In a round bottom flask 0.3 g (0.71 mmol) 2-amino-7-chloro-1-ethyl-3-[1-(2-trimethylsilanyl-ethoxymethyl)-1H-imidazol-2-yl]-1H-[1,8]naphthyridin-4-one, 0.185 g (1.07 mmol) 3-chloro-4-hydroxy-phenylboronic acid, 0.098 g (0.11 mmol) tris-(dibenzylidenacetone)dipalladium (0), 0.030 mg (0.0.11 mmol) tricyclohexyl phosphine, 0.303 g of potassium phosphate tribasic, and 8 mL of dioxane/water (50/50) (degassed) were stirred and heated at 85° C. for 8 h. The solvents were evaporated and the residue was purified by column chromatography (DCM/MeOH: 9/1) to yield 0.4 g of a brown solid. This solid was engaged without further purification in the next step.

8.2: 2-Amino-7-(3-chloro-4-hydroxy-phenyl)-1-ethyl-3-(1H-imidazol-2-yl)-1H-[1,8]naphthyridin-4-one 400 mg (0.59 mmol) of impure 2-amino-7-(3-chloro-4-hydroxy-phenyl)-1-ethyl-3-[1-(2-trimethylsilanyl-ethoxymethyl)-1H-imidazol-2-yl]-1H-[1,8]naphthyridin-4-one was dissolved in 20 ml DCM. At 0° C., 3.39 g of TFA were added and the mixture was stirred at room temperature for 24 hours. The solution is neutralized by adding an excess of aqueous $NaHCO_3$ solution. The mixture was then extracted three times with DCM. The combined organic phases were dried over $MgSO_4$ and the solvents were evaporated off under reduced pressure. The so-gained raw material was purified on silica gel (DCM:MeOH:$NH_4OH$=4:10.1) yielding 0.035 g of the unprotected title compound.
Yield for 2 steps=13%.
MH+=382 ($C_{19}H_{16}ClN_5O_2$, 381.821).
1H NMR (DMSO-d6, 400 MHz): δ 13.19 (s, 1H); 8.55 (d, 1H); 8.2 (s, 1H); 8.04 (dd, 1H); 7.9 (s, 1H); 7.15 (s, 1H); 7.09 (d, 1H); 7.3 (s, 1H); 4.72-4.66 (m, 2H); 1.37 (t, 3H).

EXAMPLE 9

Compound No 9

2-Amino-1-ethyl-7-[3-(2-fluorophenyl)-3-hydroxy-but-1-ynyl]-3-(1H-imidazol-2-yl)-1H-[1,8]naphthyridin-4-one 9.1: 2-Amino-1-ethyl-7-chloro-3-(1H-imidazol-2-yl)-1H-[1,8]naphthyridin-4-one 2-Amino-7-chloro-1-ethyl-3-[1-(2-trimethylsilanyl-ethoxymethyl)-1H-imidazol-2-yl]-1H-[1,8]naphthyridin-4-one (1.0 g, 2.38 mmol) was dissolved in 30 mL of dichoromethane. 30 mL of trifluoroacetic acid were added and the reaction mixture was stirred at room temperature for 3 h, until analytical HPLC showed complete consumption of the starting material. Solvents were removed under reduced pressure, and ethyl acetate was added to the residue. The solution was washed with saturated aqueous sodium bicarbonate. The formed precipitate was collected by filtration, then put to dry out overnight at 40° C. under vacuum, yielding 574 mg of beige powder.
Yield=83%.
1H NMR (DMSO-d6, 600 MHz): δ (ppm) 13.09 (s, 1H); 8.57 (d, 1H); 7.47 (d, 1H); 7.15 (s, 1H); 7.03 (s, 1H); 4.51 (bq, 2H); 1.29 (t, 3H).

9.2: 2-Amino-1-ethyl-7-[3-(2-fluorophenyl)-3-hydroxybut-1-ynyl]-3-(1H-imidazol-2-yl)-1H-[1,8]naphthyridin-4-one Copper (I) iodide (23.7 mg, 0.12 mmol), N-ethylmorpholine (130 μt, 1.04 mmol) and 2-(2-fluorophenyl)but-3-yn-2-ol (764, 0.52 mmol) were added to 2.5 mL of DMF. The mixture was degassed with argon. [1,1'-Bis(diphenylphosphino)ferrocene]palladium (II) chloride 1:1 complex with dichloromethane (5.6 mg, 0.01 mmol) and intermediate 20.1 (100 mg, 0.35 mmol) were added. The mixture was stirred at 80° C. under argon atmosphere for 2 h, until no remaining starting material was observed in LCMS. Ethyl acetate was added. The organic layer was successively washed with water, 1N aqueous sodium hydroxide solution, saturated aqueous sodium chloride solution, then dried over magnesium sulfate. The solvent was evaporated off under reduced pressure. The residue was then purified by column chromatography (DCM/MeOH/NH$_4$OH aq: 100/0/0→95/5/0.5) to yield 30 mg of off-white powder.

Yield=21%.
MH+=418.
Rt=0.57 min (C$_{23}$H$_{20}$FN$_5$O$_2$, 417.442).
1H NMR (DMSO-d6, 600 MHz): δ 13.10 (bs, 1H); 8.54 (d, 1H); 7.72 (dt, 1H); 7.44 (d, 1H); 7.38 (m, 1H); 7.25-7.19 (m, 2H); 7.13 (d, 1H); 7.02 (d, 1H); 6.62 (s, 1H); 4.54 (bq, 2H); 1.84 (s, 3H); 1.27 (t, 3H).

EXAMPLE 10

Compound No 12

2-Amino-7-(3-hydroxypent-1-ynyl)-3-(1H-imidazol-2-yl)-1-(2-methoxyethyl)-1H-[1,8]naphthyridin-4-one Similar procedure as that described in example 6 step 1 and 2, starting step 1 from 2-methoxyethanamine instead of cyclopropylmethylamine and then following same procedure as in example 20 step 2, starting from pent-1-yn-3-ol instead of 2-(2-fluorophenyl)but-3-yn-2-ol. 15 mg of product is obtained as a powder.

MH+=368.
Rt=0.46 min (C$_{19}$H$_{21}$N$_5$O$_3$ 367.407).

EXAMPLE 11

Compound No 19

2-Amino-1-ethyl-3-(1H-imidazol-2-yl)-7-(4,4,4-trifluoro-3-hydroxy-3-phenyl-but-1-ynyl)-1H-[1,8]naphthyridin-4-one 11.1: 2-Amino-1-ethyl-7-(4,4,4-trifluoro-3-hydroxy-3-phenyl-but-1-ynyl)-3-[1-(2-trimethylsilanyl-ethoxymethyl)-1H-imidazol-2-yl]-1H-[1,8]naphthyridin-4-one Same procedure as that described in example 5, stage 5.4, starting from 0.4 g (0.95 mmol) of 2-amino-7-chloro-1-ethyl-3-[1-(2-trimethylsilanyl-ethoxymethyl)-1H-imidazol-2-yl]-1H-[1,8]naphthyridin-4-one, 0.4 g (1.9 mmol) 1,1,1-trifluoro-2-phenyl-but-3-yn-2-ol, 33 mg (0.05 mmol), bis(triphenylphosphine)palladium(II) dichloride, 18 mg (0.1 mmol) copper (I) iodide, 3 ml DMF (degassed), 3 ml triethylamine (degassed). 0.15 g of the title compound is obtained.

Yield=30%.
MH+=584 (C$_{29}$H$_{32}$N$_5$O$_3$Si).
1H NMR (250 MHz, DMSO-d6) δ ppm 8.52 (d, J=7.91 Hz, 1H) 8.21 (s, 1H) 7.76-7.84 (m, 2H) 7.72 (br. s, 2H) 7.64 (d, J=7.91 Hz, 1H) 7.46-7.57 (m, 3H) 7.33 (d, J=1.34 Hz, 1H) 7.10 (d, J=1.34 Hz, 1H) 5.28 (s, 2H) 4.44-4.57 (m, 2H) 3.16-3.27 (m, 2H) 1.28 (t, J=6.91 Hz, 3H) 0.57-0.69 (m, 2H) −0.22 (s, 9H)

11.2: 2-Amino-1-ethyl-3-(1H-imidazol-2-yl)-7-(4,4,4-trifluoro-3-hydroxy-3-phenyl-but-1-ynyl)-1H-[1,8]naphthyridin-4-one Same procedure as that described in example 5, stage 5.5, starting from 0.145 g (0.25 mmol) of the compound obtained at the end of stage 21.1, in 1.2 ml TFA and 1.2 ml DCM, 97 mg of the title compound is obtained.

Yield=86%.
Melting point=260° C.
MH+=454 (C$_{23}$H$_{18}$F$_3$N$_5$O$_2$).
Rt=7.29 min.
1H NMR (400 MHz, DMSO-d6), δ ppm 13.12 (br. s., 1H) 11.58 (br. s., 1H) 8.63 (d, J=7.87 Hz, 1H) 8.21 (s, 1H) 8.19 (br. s, 1H) 7.77-7.82 (m, 2H) 7.66 (d, J=7.87 Hz, 1H) 7.46-7.55 (m, 3H) 7.14 (br. s., 2H) 4.57 (q, J=6.59 Hz, 2H) 1.30 (t, J=7.00 Hz, 3H)

Compounds 10 and 11 are prepared with a similar procedure as that described in example 6.

Compounds 13, 14, 15, 16, 17, 18, 20, 21, 25 are prepared with a similar procedure as that described in example 10.

Compounds 22, 23 and 24 are prepared with a similar procedure as that described in example 11.

Compound 29 is prepared with a similar procedure as that described in example 1.

Equipment Used for Examples 5 and 6
Microwave apparatus: Biotage, initiator
Analytical Method LC/UV/MS Retention Time (Rt) Detection
Analytical Method LC/UV/MS Used to Analyze Compounds (Rt) 1, 2, 3 and, 4:
Column: Merk Chromolith performance RP18e, 100×4.6 mm, 3.5 μm
Solvent A: H$_2$O/TFA (99.9/0.1)
Solvent B: ACN/TFA (99.9/0.1)
Flow rate: 2 ml/min
Gradient (A/B): 98/2 (0 min) to 0/100 (8 min) to 98/2 (10 min)
Detection: 254.16 nM
Analytical Method LC/UV/MS Used to Analyze Compound (Rt) 9, 12, 13, 14, 17, 18 and 20:
UPLC SQD Electrospray ionization, positive mode (30V)
Column: Ascentis Express 50×2.1 mm 2.7 μm, T=55° C.
Solvent A: H$_2$O+0.02% TFA
Solvent B: CH$_3$CN+0.014% TFA
Flow rate: 1 mL/min
Gradient (A/B v/v): 98/2 (t=0 min), 2/98 (t=1 min), 2/98 (t=1.3 min), 98/2 (t=1.33 min), next injection (t=1.5 min)
Detection: 220 nm
Analytical Method Used to Analyze Compounds 5, 6, 10, 11, 19, 22, 23 and 24:
HPLC chain: Series 1100, Mass spectrometer MSD SL (Agilent)
Software: Chemstation version B.01.03 from Agilent
Ionization mode: Electrospray positive mode ESI+
Mass range: 90-1500 uma
Column: Symmetry C18 3.5 μm (2.1×50 mm) (Waters) T=25° C., pH: 3
Eluents: A: H$_2$O+0.005% TFA/B: CH$_3$CN+0.005% TFA
Flow: 0.4 ml/min
Gradient: 0 to 10 min 0 to 100% B and from 10 to 15 min 100 B %
Detection: 220 nm Analytical Method LC/UV/MS Used for Compounds (Rt) 7, 8, 15, 16, 21, 25, 26:

UPLC LCT Electrospray ionization, positive mode (15V, 30V)

Software: Masslyx V4.1

Column: Acquity UPLC BEH C1850×2.1 mm 2.7 μm, T=40° C.

Solvent A: $H_2O$+0.05% TFA

Solvent B: $CH_3CN$+0.035% TFA

Flow rate: 1 mL/min

Gradient (A/B v/v): 98/2 (t=0 min), 0/100 (t=1.6 min), 0/100 (t=2.1 min), 98/2 (t=2.5 min), next injection (t=3 min)

Detection: at 220 nm

NMR

The 1H NMR spectra were obtained using NMR spectrometers Bruker 250, 300, 400, or 600 MHz in DMSO-d6, using the peak of DMSO-d5 as internal reference. The chemical shifts δ expressed in parts per million (ppm).

The signals observed are expressed as follows: s=singlet; d=doublet; t=triplet; q=quadruplet; m=multiplet or large singlet; br=broad; H=proton.

Melting Points

The melting points below 260° C. were measured with a Kofler bench and melting points above 260° C. were measured with a Buchi B-545 instrument.

Rotatory Powers

The rotatory powers were measured on a polarimeter of the type: Polarimeter Perkin-Elmer, energy 55 μA.

TABLE 1

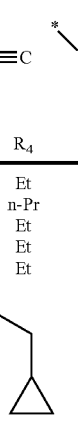

| Compound | W | Y | $R_1$ | $R_2$ | $R_3$ | $R_4$ | $R_5$ | Chirality | LCMS: MH+ (Rt) |
|---|---|---|---|---|---|---|---|---|---|
| 1 | N | C≡C | —$CH_2OCH_3$ | Me | H | Et | H | R | 368.2 (0.59 min) |
| 2 | N | C≡C | —$CH_2OCH_3$ | Me | H | n-Pr | H | R | 382.5 (1.0 min) |
| 3 | N | C≡C | —$CH_2OH$ | Me | H | Et | H | Rac. | 354.16 (0.78 min) |
| 4 | N | C≡C | -3-pyridyl | Me | H | Et | H | Rac. | 401.21 (1.85 min) |
| 5 | N | C≡C | —$CH_2OCH_3$ | Me | H | Et | Me | R | 382 (1.01 min) |
| 6 | N | C≡C | Et | H | H | 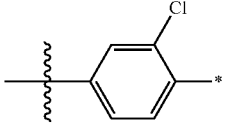 | H | Rac. | 364 (5.96 min) |
| 7 | CH | C≡C | —$CH_2OCH_3$ | Me | H | Et | H | R | 367 (0.58 min) |
| 8 | N |  | Bond | | H | Et | H | | 382 (1.26 min) |
| 9 | N | C≡C | 2-fluoro-phenyl | Me | H | Et | H | Rac. | 418 (0.57 min) |
| 10 | N | C≡C | H | Et | H | 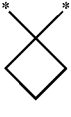 | H | Rac. | 378 (0.57 min) |
| 11 | N | C≡C | Et | H | H | —$(CH_2)_3OCH_3$ | H | Rac. | 382 (6.32 min) |
| 12 | N | C≡C | Et | H | H | —$(CH_2)_2OCH_3$ | H | Rac. | 368 (5.64 min) |
| 13 | N | C≡C |  | | H | Et | H | | 350 (0.47 min) |
| 14 | N | C≡C |  | | H | Et | H | | 364 (0.5 min) |

TABLE 1-continued

[Structure diagram showing compound with substituents R3, R4, R5, W, Y, Z, NH2, and note: If Y = C≡C, Z = *\Z/* or *\C(R1)(R2)/*]

| Compound | W | Y | R₁ | R₂ | R₃ | R₄ | R₅ | Chirality | LCMS: MH+ (Rt) |
|---|---|---|---|---|---|---|---|---|---|
| 15 | N | C≡C | Me | Me | H | Et | H | | 338 (0.63 min) |
| 16 | N | C≡C | Me | Et | H | Et | H | Rac. | 352 (0.67 min) |
| 17 | N | C≡C | phenyl | Me | H | Et | H | Rac. | 400 (0.57 min) |
| 18 | N | C≡C | 3-fluoro-phenyl | Me | H | Et | H | Rac. | 418 (0.59 min) |
| 19 | N | C≡C | phenyl | CF₃ | H | Et | H | Rac. | 453 (7.73 min) |
| 20 | N | C≡C | cycloypropyl | Me | H | Et | H | Rac. | 364 (0.49 min) |
| 21 | N | C≡C | 2-thienyl | Me | H | Et | H | Rac. | 406 (1.19 min) |
| 22 | N | C≡C | H | Me | H | Et | H | Rac. | 324 (4.82 min) |
| 23 | N | C≡C | H | Et | H | Et | H | Rac. | 338 (5.26 min) |
| 24 | N | C≡C | n-propyl | H | H | Et | H | Rac. | 352 (5.81 min) |
| 25 | N | C≡C | isopropyl | H | H | Et | H | Rac. | 352 (0.69 min) |
| 26 | N | C≡C | phenyl | H | H | Et | H | Rac. | 386 (0.74 min) |
| 27 | N | C≡C | —CH₂OH | Me | H | Et | H | R | 354.16 (0.77 min) |
| 28 | N | C≡C | —CH₂OH | Me | H | Et | H | S | 354.16 (0.77 min) |
| 29 | N | C≡C | —CH₂OCH₃ | Me | H | Et | H | S | 368.2 (0.59 min) |

The compounds according to the invention were the subject of pharmacological assays for determining their inhibitory effect on autophosphorylation of VEGFR-3 as well as to evaluate their ex vivo activity described in the assay below.

Effect of Compounds on VEGFR-3 Auto-Phosphorylation in HEK Cells

The effects of compounds in blocking VEGFR-3 autophosphorylation were quantified by ELISA after Overexpression of VEGFR-3 in HEK cells. HEK293T cells were maintained in MEM supplemented with 10% foetal calf serum (FCS) and glutamine. The day before transfection, 104 cells/well were seeded on 48 wells plates and transfection was done using Fugene-6 (Roche, Basel). Fugene-6 (18 μL) was preincubated for 5 min with 282 μA of optimem. Then 3 μg DNA corresponding VFGR-3-Flag was added and left at room temperature during 10 min before distributing 200 μl on HEK cells. After 24 h, the medium was removed and replaced by a new one without serum and incubated for 1 h with different concentrations (ranging from 3 to 1000 nM) of each compound. After additional 30 min incubation with Orthovanadate (0.4 mM), cells were washed with cold PBS supplemented by orthovanadate and then lysed with 300 μA of RIPA buffer. Lysates were then centrifuged during 10 min at 10000 g. Supernatants (75 μl) were distributed in duplicate on 96 well plate precoated with the anti-Flag and left during 1 hour at room temperature. After 3 washes with TBS buffer containing 0.5% tween20, the anti-phospho-tyrosine conjugated to the HRP was added and incubated for 1 hour at room temperature. Wells were then washed 3 times with TBS buffer containing tween 20 (0.5%) and MgCl₂ (2 mM). The reaction was stopped with 50 μA of H₂SO₄ (2 N) and the signal was read at Envision at 485 and 530.

The concentration-response curves were analyzed with internal software Biost@t-SPEED v2.0 using the 4-parameter logistic model according to Ratkovsky and Reedy (Ratkovsky D A., Reedy T J. Choosing near-linear parameters in the four parameters logistic model radioligands and related assays. Biometrics 1986 September 42(3):575-82.)

The compounds according to the invention have an inhibitory activity on the autophosphorylation of VEGFR-3 and exhibiting $IC_{50}$ values of less than 1 μM in the autophosphorylation in HEK cells, particularly between 1 and 500 nM, more particularly between 1 and 100 nM.

By way of examples, the $IC_{50}$ values of some compounds of Table 1 are indicated in Table 2 below.

TABLE 2

| No. of the compound | $IC_{50}$ (nM) |
|---|---|
| 1 | 25 |
| 2 | 18 |
| 3 | 125 |
| 4 | 40 |
| 5 | 45 |
| 6 | 85 |
| 7 | 19 |
| 8 | 73 |
| 9 | 16 |
| 10 | 37 |
| 11 | 334 |
| 12 | 166 |
| 13 | 41 |
| 14 | 200 |
| 15 | 27 |
| 16 | 119 |
| 17 | 13 |
| 18 | 36 |
| 19 | 14 |
| 21 | 24 |
| 22 | 38 |
| 23 | 19 |
| 24 | 85 |
| 25 | 303 |
| 26 | 120 |
| 27 | 47 |
| 28 | 153 |
| 29 | 145 |

The inhibitors of VEGFR-3 tyronise kinase according to the invention present a good ex vivo activity using an assay measuring the inhibition of autophosphorylation of VEGFR3, even better that the one of the inhibitors of the prior art.

of the invention, a comparison with compounds of the prior art (WO 2009/007535) and subjected to the same measurement is made in table 3.

TABLE 3

Comparison of ex vivo activity between of compounds from this invention and the corresponding compound of the prior art after p.o administration to male Balb/c mice

| Ex | W | Y | R¹ | R² | R³ | R⁴ | R⁵ | Chirality | A | Ex vivo inhibition (%) At the time |
|----|---|---|----|----|----|----|----|-----------|---|------|
| 1  | N | C≡C | —CH₂OCH₃ | Me | H | Et | H | R | Imidazole | 83%, 6 h |
| 1' |   |   |    |    |    |    |   |   | Amide | 40%, 6 h |
| 3  | N | C≡C | —CH₂OH | Me | H | Et | H | Rac. | Imidazole | 51%, 3 h |
| 3' |   |   |    |    |    |    |   |   | Amide | 0%, 3 h |
| 4  | N | C≡C | -3-pyridyl | Me | H | Et | H | Rac. | Imidazole | 28%, 6 h |
| 4' |   |   |    |    |    |    |   |   | Amide | 0%, 6 h |
| 5  | N | C≡C | —CH₂OCH₃ | Me | H | Et | Me | R | Imidazole | 86%, 6 h |
| 5' |   |   |    |    |    |    | H |   | Amide | 40% 6 h |
| 13 | N | C≡C | *⟨⟩* |    | H | Et | H |   | Imidazole | 23%, 6 h |
| 13'|   |   |    |    |    |    |   |   | Amide | 17%, 6 h |
| 16 | N | C≡C | Me | Et | H | Et | H | Rac. | Imidazole | 48%, 3 h |
| 16'|   |   |    |    |    |    |   |   | Amide | 20%, 3 h |
| 17 | N | C≡C | phenyl | Me | H | Et | H | Rac. | Imidazole | 37%, 6 h |
| 17'|   |   |    |    |    |    |   |   | Amide | 5%, 6 h |
| 22 | N | C≡C | H | Me | H | Et | H | Rac. | Imidazole | 26%, 6 h |
| 22'|   |   |    |    |    |    |   |   | Amide | 0%, 3 h |

Ex Vivo Assay

Protocol for administration of the products to the mice:

The products are prepared in a mortar with 0.5% Tween 80 and 0.6% methylcellulose qs final volume. The suspensions are administered by gavage (10 ml/kg) to male Balb/c mice 8 to 15 weeks old. Three hours or 6 hours after single oral administrations of 30 mg/kg, animals were anaesthetized with pentobarbital and blood samples (400 µL) were collected from cava vein and transferred into glass tubes containing lithium heparin. After centrifugation (1500-2000 g for 10 minutes), plasma samples were frozen at a temperature close to −20° C. until analysis.

In order to detect the ex vivo activity of the products in the plasmas, we have used the autophosphorylation assay in HEK cells described earlier. For this purpose, transfected cells were incubated with plasma (10%) instead of compounds. Results are expressed as percent of inhibition of VEGFR-3 autophosphorylation in comparison to untreated cells (maximum autophosphorylation) and to untransfected cells (background).

The ex vivo activity of the compounds of the invention are summarized in the following table 3. Results are expressed as a percentage of inhibition of VEGFR-3 auto-phosphorylation of in HEK cells, in presence of a plasma sample collected (at a time), after per os (p.o.) administration of compounds. In order to evaluate the increase of this activity for compounds It therefore appears that compounds according to the invention have an inhibitory activity on the autophosphorylation of VEGFR-3, they may therefore be used in the preparation of medicaments, in particular of medicaments which inhibit VEGFR-3.

The increase of exposure of the compound particularly the bio availability is one of the criterium for the increase in the ex vivo inhibition of the autophosphorylation of VEGFR3 of compound of the invention.

The inhibitors of VEGFR-3 tyronise kinase according to the invention present a good bioavailability, even better that the one of the inhibitors of the prior art.

The bioavailability refers to the extent to and rate at which the active moiety (drug or metabolite) enters systemic circulation, thereby accessing the site of action.

Bioavailability of a drug is largely determined by the properties of the dosage form (which depend partly on its design and manufacture), rather than by the drug's physicochemical properties, which determine absorption potential. Differences in bioavailability among formulations of a given drug can have clinical significance; thus, knowing whether drug formulations are equivalent is essential.

The bioavailability is used to describe the fraction of an administered dose of unchanged drug that reaches the systemic circulation, one of the principal pharmacokinetic properties of drugs. By definition, when a medication is administered intravenously, its bioavailability is 100%. However, when a medication is administered via other routes (such as orally), its bioavailability decreases (due to incomplete absorption and first-pass metabolism) or may vary from patient to patient (due to inter-individual variation). Bioavailability is one of the essential tools in pharmacokinetics, as bioavailability must be considered when calculating dosages for non-intravenous routes of administration.

Thus, according to another of its aspects, a subject of the invention is medicaments which comprise a compound of formula (I), or an addition salt of the latter with a pharmaceutically acceptable acid or base, and also an enantiomer or a diastereoisomer, including a mixture thereof, of the compound of formula (I).

Another aspect of the invention comprises a combination of at least one compound according to the invention and at least one therapeutic agent.

Specifically, the compounds of the present invention may be used alone or as a mixture with at least one therapeutic agent that may be selected from:
  alkylating agents,
  intercalating agents,
  antimicrotubule agents,
  antimitotics,
  antimetabolites,
  antiproliferative agents,
  antibiotics,
  immunomodulatory agents,
  anti-inflammatories,
  kinase inhibitors,
  anti-angiogenic agents,
  antivascular agents,
  oestrogenic and androgenic hormones.

It is also possible to combine the compounds according to the invention with a radiation treatment.

The combinations of the compounds of the invention with the therapeutic agents mentioned above and/or radiation are another subject of the present invention.

The therapeutic agents mentioned above and/or the radiation may be administered simultaneously, separately or sequentially. The treatment will be adjusted by the practitioner according to the patient to be treated.

These medicaments are used therapeutically, in particular in the treatment and/or prevention:
  of cancers and metastases thereof, such as glioblastomas, multiple myelomas, myelodysplasic syndromes, Kaposi's sarcomas, cutaneous angiosarcomas, solid tumours, lymphomas, melanomas, breast cancers, colorectal cancers, lung cancers, including non-small-cell cancers, pancreatic cancers, prostate cancers, kidney cancers, head and neck cancers, liver cancers, ovarian cancers, cancers of the respiratory tract and chest, other tumours expressing VEGFR-3 or involving a process of angiogenesis or of lymphangiogenesis,
  of non-oncological proliferative diseases and pathological angiogenesis linked to VEGFR-3, such as arthrosis, restenosis, psoriasis, hemangiomas, lymphangiomas, glaucomas, glomerulonephritis, diabetic nephropathies, nephrosclerosis, thrombotic microangiopathic syndromes, liver cirrhosis, atherosclerosis, organ transplant rejection, eye diseases involving a process of angiogenesis or of lymphangiogenesis, such as diabetic retinopathy or macular degeneration,
  or else in the treatment and prevention of inflammation (chronic or non-chronic), of infection with microorganisms and of autoimmune diseases, such as rheumatoid arthritis,
  or else in the treatment of rare diseases such as lymphangioleiomyomatosis.

According to another of its aspects, the present invention relates to pharmaceutical compositions comprising, as active ingredient, a compound according to the invention. These pharmaceutical compositions contain an effective dose of at least one compound according to the invention, or a pharmaceutically acceptable salt, a hydrate or a solvate of said compound, and also at least one pharmaceutically acceptable excipient.

Said excipients are selected according to the pharmaceutical form and the method of administration desired, from the usual excipients which are known to those skilled in the art.

In the pharmaceutical compositions of the invention for oral, sublingual, subcutaneous, intramuscular, intravenous, topical, local, intratracheal, intranasal, transdermal or rectal administration, the active ingredient of formula (I) above, or possible salt, solvate or hydrate thereof, may be administered in unit administration form, as a mixture with conventional pharmaceutical excipients, to animals and to human beings for the treatment or prevention of the disorders or diseases above.

The appropriate unit administration forms comprise oral administration forms, such as tablets, soft or hard gel capsules, powders, granules and oral solutions or suspensions, sublingual, buccal, intratracheal, intraocular and intranasal administration forms, forms for administration by inhalation, topical, transdermal, subcutaneous, intramuscular or intravenous administration forms, rectal administration forms, and implants. For topical application, the compounds according to the invention can be used in creams, gels, ointments or lotions.

By way of example, a unit form of administration of a compound according to the invention in tablet form may comprise the following components:

| | |
|---|---|
| Compound according to the invention | 50.0 mg |
| Mannitol | 223.75 mg |
| Croscarmellose sodium | 6.0 mg |
| Corn starch | 15.0 mg |
| Hydroxypropylmethylcellulose | 2.25 mg |
| Magnesium stearate | 3.0 mg |

According to another its aspects, the present invention also relates to a method of treating the pathologies indicated above, which comprises the administration, to a patient, of an effective dose of a compound according to the invention, or a pharmaceutically acceptable salt thereof.

The invention claimed is:

1. A compound of formula (I):

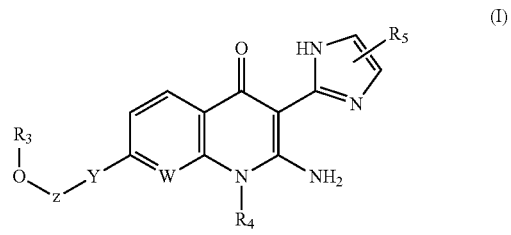

in which:
W represents a nitrogen atom or a group CH;
Y represents a group $C_2$-$C_3$-alkynylene or a 1,4-phenylene optionally substituted with $R_7$ which represents one or more halogen atom(s);
Z represents a bond or a group $CR_1R_2$;
$R_1$ and $R_2$, independently of each other, represent a group chosen from a hydrogen atom, a group $C_1$-$C_6$-alkyl, a trifluoromethyl group, a group $(CH_2)_nOR_6$, $C_3$-$C_7$-cycloalkyl, an heteroaryl or an aryl optionally substituted with one or more halogen atom(s);
or $R_1$ and $R_2$ can form together, with the carbon atom which bear them, a $C_3$-$C_7$-cycloalkyl;
$R_3$ represents a hydrogen atom;
$R_4$ represents a group chosen from a group $C_1$-$C_6$-alkyl, a group $(CH_2)_nOR_6$, $C_3$-$C_7$-cycloalkyl or $C_1$-$C_6$-alkyl optionally substituted by a $C_3$-$C_7$-cycloalkyl;
$R_5$ represents a group chosen from a hydrogen atom or a group $C_1$-$C_6$-alkyl;
$R_6$ represents a group chosen from a hydrogen atom or a group $C_1$-$C_6$-alkyl;
n is equal to 1, 2 or 3;
in the form of the base or of an acid-addition salt.

2. The compound according to claim 1, wherein W represents a a group CH, in the form of the base or of an acid-addition salt.

3. The compound according to claim 1, wherein W represents a nitrogen atom, in the form of the base or of an acid-addition salt.

4. The compound according to claim 1, wherein Y represents a group $C_2$-$C_3$-alkynylene in the form of the base or of an acid-addition salt.

5. The compound according to claim 1, wherein
$R_1$ represents a group chosen from a hydrogen atom, a group $C_1$-$C_6$-alkyl, a group $(CH_2)_nOR_6$, $C_3$-$C_7$-cycloalkyl, an aryl or a 5- or 6-membered-heteroaryl;
$R_2$ represents a group chosen from a hydrogen atom, a group $C_1$-$C_6$-alkyl or a trifluoromethyl;
in the form of the base or of an acid-addition salt.

6. The compound according to claim 1, wherein
Z represents a group $CR_1R_2$;
$R_1$ represents a group chosen from a hydrogen atom, a group $C_1$-$C_6$-alkyl, a group $(CH_2)_nOR_6$, $C_3$-$C_7$-cycloalkyl, an aryl or a 5- or 6-membered-heteroaryl;
$R_2$ represents a group chosen from a hydrogen atom, a group $C_1$-$C_6$-alkyl or a trifluoromethyl;
in the form of the base or of an acid-addition salt.

7. The compound according to claim 1, wherein $R_4$ represents a group chosen from a group $(CH_2)_nOR_6$, $C_3$-$C_7$-cycloalkyl or $C_1$-$C_6$-alkyl optionally substituted by a $C_3$-$C_7$-cycloalkyl, in the form of the base or of an acid-addition salt.

8. The compound according to claim 1, wherein $R_4$ represents a group $C_1$-$C_6$-alkyl, in the form of the base or of an acid-addition salt.

9. The compound according to claim 1, wherein $R_5$ represents a group $C_1$-$C_6$-alkyl, in the form of the base or of an acid-addition salt.

10. The compound according to claim 1, wherein $R_5$ represents a hydrogen atom, in the form of the base or of an acid-addition salt.

11. The compound according to claim 1, wherein
Y represents a group $C_2$-$C_3$-alkynylene or a 1,4-phenylene optionally substituted with $R_7$ which represents a halogen atom;
$R_1$ represents a group chosen from a hydrogen atom, a group $C_1$-$C_6$-alkyl, a group $(CH_2)_nOR_6$, $C_3$-$C_7$-cycloalkyl, an aryl or a 5- or 6-membered-heteroaryl optionally substituted with a halogen atom;
$R_2$ represents a group chosen from a hydrogen atom, a group $C_1$-$C_6$-alkyl or a trifluoromethyl;
in the form of the base or of an acid-addition salt.

12. The compound according to claim 1, wherein $R_1$ and $R_2$ form together, with the carbon atom which bear them, a $C_3$-$C_7$-cycloalkyl, in the form of the base or of an acid-addition salt.

13. The compound according to claim 1, in the form of the base or of an acid-addition salt, chosen from the group consisting of:
2-Amino-1-ethyl-7-((3R)-3-hydroxy-4-methoxy-3-methyl-but-1-ynyl)-3-(1H-imidazol-2-yl)-1H-[1,8]naphthyridin-4-one;
2-Amino-1-propyl-7-((3R)-3-hydroxy-4-methoxy-3-methyl-but-1-ynyl)-3-(1H-imidazol-2-yl)-1H-[1,8]naphthyridin-4-one;
2-Amino-7-(3,4-dihydroxy-3-methyl-but-1-ynyl)-1-ethyl-3-(1H-imidazol-2-yl)-1H-[1,8]naphthyridin-4-one;
2-Amino-1-ethyl-7-(-3-hydroxy-3-pyridin-2-yl-but-1-ynyl)-3-(1H-imidazol-2-yl)-1H-[1,8]naphthyridin-4-one;
2-Amino-1-ethyl-7-[(3R)-3-hydroxy-4-methoxy-3-methyl-but-1-ynyl]-3-(4-methyl-1H-imidazol-2-yl)-1H-[1,8]naphthyridin-4-one;
2-Amino-1-(cyclopropylmethyl)-7-(3-hydroxy-pent-1-ynyl)-3-(1H-imidazol-2-yl)-1H-[1,8]naphthyridin-4-one;
2-Amino-1-ethyl-7-[(3R)-3-hydroxy-4-methoxy-3-methyl-but-1-ynyl]-3-(1H-imidazol-2-yl)-1H-quinolin-4-one;
2-Amino-7-(3-chloro-4-hydroxy-phenyl)-1-ethyl-3-(1H-imidazol-2-yl)-1H-[1,8]naphthyridin-4-one;
2-Amino-1-ethyl-7-[3-(2-fluorophenyl)-3-hydroxy-but-1-ynyl]-3-(1H-imidazol-2-yl)-1H-[1,8]naphthyridin-4-one;
2-Amino-1-cyclopentyl-7-(3-hydroxy-pent-1-ynyl)-3-(1H-imidazol-2-yl)-1H-[1,8]naphthyridin-4-one;
2-Amino-7-(3-hydroxy-pent-1-ynyl)-3-(1H-imidazol-2-yl)-1-(3-methoxypropyl)-1H-[1,8]naphthyridin-4-one;
2-Amino-7-(3-hydroxy-pent-1-ynyl)-3-(1H-imidazol-2-yl)-1-(2-methoxyethyl)-1H-[1,8]naphthyridin-4-one;
2-Amino-1-ethyl-7-[(1-hydroxycyclobutyl)ethynyl]-3-(1H-imidazol-2-yl)-1H-[1,8]naphthyridin-4-one;
2-Amino-1-ethyl-7-[(1-hydroxycyclopentyl)ethynyl]-3-(1H-imidazol-2-yl)-1H-[1,8]naphthyridin-4-one;
2-Amino-1-ethyl-7-(3-hydroxy-3-methyl-but-1-ynyl)-3-(1H-imidazol-2-yl)-1H-[1,8]naphthyridin-4-one;
2-Amino-1-ethyl-7-(3-hydroxy-3-methyl-pent-1-ynyl)-3-(1H-imidazol-2-yl)-1H-[1,8]naphthyridin-4-one;
2-Amino-1-ethyl-7-(3-hydroxy-3-phenyl-but-1-ynyl)-3-(1H-imidazol-2-yl)-1H-[1,8]naphthyridin-4-one;
2-Amino-1-ethyl-7-[3-(3-fluorophenyl)-3-hydroxy-but-1-ynyl]-3-(1H-imidazol-2-yl)-1H-[1,8]naphthyridin-4-one;
2-Amino-1-ethyl-3-(1H-imidazol-2-yl)-7-(4,4,4-trifluoro-3-hydroxy-3-phenyl-but-1-ynyl)-1H-[1,8]naphthyridin-4-one;
2-Amino-7-(3-cyclopropyl-3-hydroxy-but-1-ynyl)-1-ethyl-3-(1H-imidazol-2-yl)-1H-[1,8]naphthyridin-4-one;
2-Amino-1-ethyl-7-[3-hydroxy-3-(thiophen-2-yl)but-1-ynyl]-3-(1H-imidazol-2-yl)-1H-[1,8]naphthyridin-4-one;

2-Amino-1-ethyl-7-(3-hydroxy-but-1-ynyl)-3-(1H-imidazol-2-yl)-1H-[1,8]naphthyridin-4-one;
2-Amino-1-ethyl-7-(3-hydroxy-pent-1-ynyl)-3-(1H-imidazol-2-yl)-1H-[1,8]naphthyridin-4-one;
2-Amino-1-ethyl-7-(3-hydroxy-hex-1-ynyl)-3-(1H-imidazol-2-yl)-1H-[1,8]naphthyridin-4-one;
2-Amino-1-ethyl-7-(3-hydroxy-4-methyl-pent-1-ynyl)-3-(1H-imidazol-2-yl)-1H-[1,8]naphthyridin-4-one;
2-Amino-1-ethyl-7-(3-hydroxy-3-phenyl-prop-1-ynyl)-3-(1H-imidaz ol-2-yl)-1H-[1,8]naphthyridin-4-one;
2-Amino-7-((3R)3,4-dihydroxy-3-methyl-but-1-ynyl)-1-ethyl-3-(1H-imidazol-2-yl)-1,8-naphthyridin-4(1H)-one;
2-Amino-7-((3S)3,4-dihydroxy-3-methyl-but-1-ynyl)-1-ethyl-3-(1H-imidazol-2-yl)-1, 8-naphthyridin-4(1H)-one; and
2-Amino-1-ethyl-7-((3S)-3-hydroxy-4-methoxy-3-methyl-but-1-ynyl)-3-(1H-imidazol-2-yl)-1,8-naphthyridin-4(1H)-one.

14. A process for preparing the compound according to claim 1, comprising reacting a compound of formula (VII):

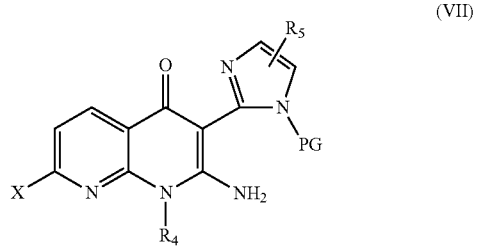

(VII)

in which X is a chlorine or a bromine and $R_4$ and $R_5$ are as defined in claim 1 with a compound of general formula (XVa):

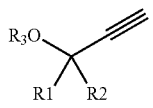

(XVa)

in which $R_1$, $R_2$ and $R_3$ are as defined in claim 1,
or with a compound of general formula (XVb):

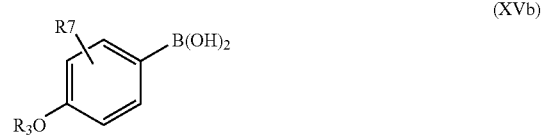

in which R3 and R7 are as defined in claim 1,
and carrying out a conventional stage of deprotection before or after reacting the compound of formula (VII) with the compound of general formula (XVa) or the compound of general formula (XVb).

15. A pharmaceutical composition comprising the compound of claim 1, or a pharmaceutically acceptable salt, or an enantiomer or a diastereoisomer, or a mixture thereof.

16. The pharmaceutical composition of claim 15 further comprising at least one pharmaceutically acceptable excipient.

17. The combination of the compound according to claim 1 with at least one therapeutic agent selected from:
   alkylating agents,
   intercalating agents,
   antimicrotubule agents,
   antimitotics,
   antimetabolites,
   antiproliferative agents,
   antibiotics,
   immunomodulatory agents,
   anti-inflammatories,
   kinase inhibitors,
   anti-angiogenic agents,
   antivascular agents,
   oestrogenic and androgenic hormones.

18. The compound according to claim 4, wherein said $C_2$-$C_3$-alkynylene is ethynylene.

19. The compound according to claim 8, wherein said group $C_1$-$C_6$ alkyl is an ethyl.

* * * * *

UNITED STATES PATENT AND TRADEMARK OFFICE
CERTIFICATE OF CORRECTION

PATENT NO. : 9,126,972 B2  
APPLICATION NO. : 14/117750  
DATED : September 8, 2015  
INVENTOR(S) : Alain Braun et al.

Page 1 of 1

It is certified that error appears in the above-identified patent and that said Letters Patent is hereby corrected as shown below:

In the Claims:

At column 37, claim number 1, line 6: please replace "Z" with --z--;

At column 37, claim number 2, line 26: please replace "a a group" with --a group--;

At column 37, claim number 6, line 42: please replace "Z" with --z--;

At column 38, claim number 13, lines 23-25: please replace "2-Amino-1-ethyl-7-(-3-hydroxy-3-pyridin-2-yl-but-1-ynyl)-3-(1H-imidazol-2-yl)-1H-[1,8]naphthyridin-4-one;" with --2-Amino-1-ethyl-7-(3-hydroxy-3-pyridin-2-yl-but-1-ynyl)-3-(1H-imidazol-2-yl)-1H-[1,8] naphthyridin-4-one;--;

At column 39, claim number 13, lines 9-10: please replace "2-Amino-1-ethyl-7-(3-hydroxy-3-phenyl-prop-1-ynyl)-3-(1H-imidaz ol-2-yl)-1H-[1,8]naphthyridin-4-one;" with --2-Amino-1-ethyl-7-(3-hydroxy-3-phenyl-prop-1-ynyl)-3-(1H-imidazol-2-yl)-1H-[1,8]naphthyridin-4-one;--; and At column 39, claim number 13, lines 14-16: please replace "2-Amino-7-((3S)3,4-dihydroxy-3-methyl-but-1-ynyl)-1-ethyl-3-(1H-imidazol-2-yl)-1, 8-naphthyridin-4(1H)-one;" with --2-Amino-7-((3S)3,4-dihydroxy-3-methyl-but-1-ynyl)-1-ethyl-3-(1H-imidazol-2-yl)-1,8-naphthyridin-4(1H)-one--.

Signed and Sealed this  
Fifth Day of April, 2016

Michelle K. Lee  
*Director of the United States Patent and Trademark Office*